United States Patent
Takakura et al.

(10) Patent No.: US 12,312,603 B2
(45) Date of Patent: May 27, 2025

(54) CELL POPULATIONS OF CD31-POSITIVE, CD45-NEGATIVE, CD200-POSITIVE MAMMALIAN CELLS AND USE THEREOF

(71) Applicant: Osaka University, Osaka (JP)

(72) Inventors: Nobuyuki Takakura, Osaka (JP); Hisamichi Naito, Osaka (JP); Taku Wakabayashi, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 18/424,597

(22) Filed: Jan. 26, 2024

(65) Prior Publication Data

US 2024/0279616 A1     Aug. 22, 2024

Related U.S. Application Data

(62) Division of application No. 16/763,938, filed as application No. PCT/JP2018/042255 on Nov. 15, 2018, now Pat. No. 11,920,161.

(30) Foreign Application Priority Data

Nov. 17, 2017   (JP) .................................. 2017-221955

(51) Int. Cl.
| | | |
|---|---|---|
| C12N 5/071 | (2010.01) | |
| A61K 35/44 | (2015.01) | |
| A61P 1/16 | (2006.01) | |
| A61P 7/04 | (2006.01) | |
| G01N 33/50 | (2006.01) | |

(52) U.S. Cl.
CPC ............ *C12N 5/0692* (2013.01); *A61K 35/44* (2013.01); *A61P 1/16* (2018.01); *A61P 7/04* (2018.01); *G01N 33/5073* (2013.01); *C12N 2509/10* (2013.01)

(58) Field of Classification Search
CPC .................. C12N 5/0692; C12N 5/0081–0696
See application file for complete search history.

(56) References Cited

U.S. PATENT DOCUMENTS

| | | |
|---|---|---|
| 2013/0225443 A1 | 8/2013 | Osafune et al. |
| 2016/0038545 A1 | 2/2016 | Patel et al. |
| 2019/0151373 A1 | 5/2019 | Patel et al. |

FOREIGN PATENT DOCUMENTS

| | | |
|---|---|---|
| JP | 2013-544089 A | 12/2013 |
| WO | WO 2009/010885 A2 | 1/2009 |
| WO | WO 2014/138793 A1 | 9/2014 |

OTHER PUBLICATIONS

Communication pursuant to Article 94(3) EPC in EP Application No. 18878102.5 dated Nov. 29, 2024.

Barcia, Rita N. et al., "Umbilical cord tissue-derived mesenchymal stromal cells maintain immunomodulatory and angiogenic potencies after cryopreservation and subsequent thawing" Cytotherapy, 2017, pp. 360-370, vol. 19.
Belkin, Daniel A. et al., "CD200 Upregulation in Vascular Endothelium Surrounding Cutaneous Squamous Cell Carcinoma" JAMA Dermatol., Feb. 2013, pp. 178-186, vol. 149, No. 23.
Kikuchi, Emiko et al., "2. SCRG1 Maintains the Stemness of Mesenchymal Stem Cells via the Receptor BST1/CD157" Dental Journal of Iwate Medical University, 2015, p. 94, vol. 40, No. 2.
Lu, W. et al., "Improved Proliferation and Differentiation of Bone Marrow Mesenchymal Stem Cells Into Vascular Endothelial Cells With Sphingosine 1-Phosphate" Transplantation Proceedings, 2015, pp. 2035-2040, vol. 47.
Naito, Hisamichi et al., "Identification and characterization of a resident vascular stem/progenitor cell population in preexisting blood vessels" The EMBO Journal, 2012, pp. 842-855, vol. 31, No. 4.
Naito, Hisamichi et al., "Endothelial Side Population Cells Contribute to Tumor Angiogenesis and Antiangiogenic Drug Resistance" Cancer Research, Jun. 2016, pp. 3200-3210, vol. 76, No. 11.
Takahashi, Tomono et al., "Ischemia- and cytokine-induced mobilization of bone marrow-derived endothelial progenitor cells for neovascularization" Nature Medicine, Apr. 1999, pp. 434-438, vol. 5, No. 4.
Takakura, Nobuyuki "Discovery of vascular resident endothelial stem/progenitor cell population" Japanese Journal of Thrombosis and Hemostasis, 2014, pp. 603-608, vol. 25, No. 5.
Wakabayashi, Taku et al., "Identification of Vascular Endothelial Side Population Cells in the Choroidal Vessels and Their Potential Role in Age-Related Macular Degeneration" Invest Ophthalmol Vis Sci., Oct. 2013, pp. 6686-6693, vol. 54, No. 10.
Wakabayashi, Taku et al., "CD157 Marks Tissue-Resident Endothelial Stem Cells with Homeostatic and Regenerative Properties" Cell Stem Cell, Mar. 2018, pp. 384-397, vol. 22.
Wakabayashi, Taku et al., "Identification of resident vasculoreparative endothelial stem cells responsible for ocular angiogenesis", Investigative Ophthalmology & Visual Science, Jul. 2018, vol. 59, No. 9.
International Search Report for PCT/JP2018/042255 dated Feb. 12, 2019.
International Preliminary Report on Patentability dated Apr. 8, 2020 for International Application No. PCT/JP2018/042255, in 14 pages.
Supplementary European Search Report for EP 18878102 dated Dec. 7, 2020.

(Continued)

*Primary Examiner* — Thane Underdahl
(74) *Attorney, Agent, or Firm* — Knobbe Martens Olson & Bear LLP

(57) ABSTRACT

Provided are a cell population substantially consisting of mammalian cells that are positive for cell surface markers CD31 and CD200 and negative for CD45; a cell population substantially consisting of mammalian cells that are positive for cell surface markers CD31, CD157 and CD200 and negative for CD45; a mammalian vascular endothelial stem cell that is positive for the cell surface marker CD31, positive for at least one of CD157 and CD200, and negative for CD45; and a medicament for vascular regeneration, comprising any of the cell populations or the vascular endothelial stem cells as an active ingredient.

16 Claims, 9 Drawing Sheets

Specification includes a Sequence Listing.

(56) References Cited

OTHER PUBLICATIONS

Office Action for CN 201880073912.8 issued Jul. 27, 2022.
Office Action for JP 2019-554274 issued Aug. 23, 2022.
Communication pursuant to Article 94(3) EPC for EP 18878102.5 issued Jan. 25, 2023.
Second Office Action for CN 201880073912.8 issued Apr. 21, 2023.
Examination Report No. 1 for AU 2018367552 issued on Mar. 28, 2024.
Examination Report No. 2 for AU 2018367552 issued on Aug. 28, 2024.
Office Action for CA 3,082,528 issued on Sep. 26, 2024.

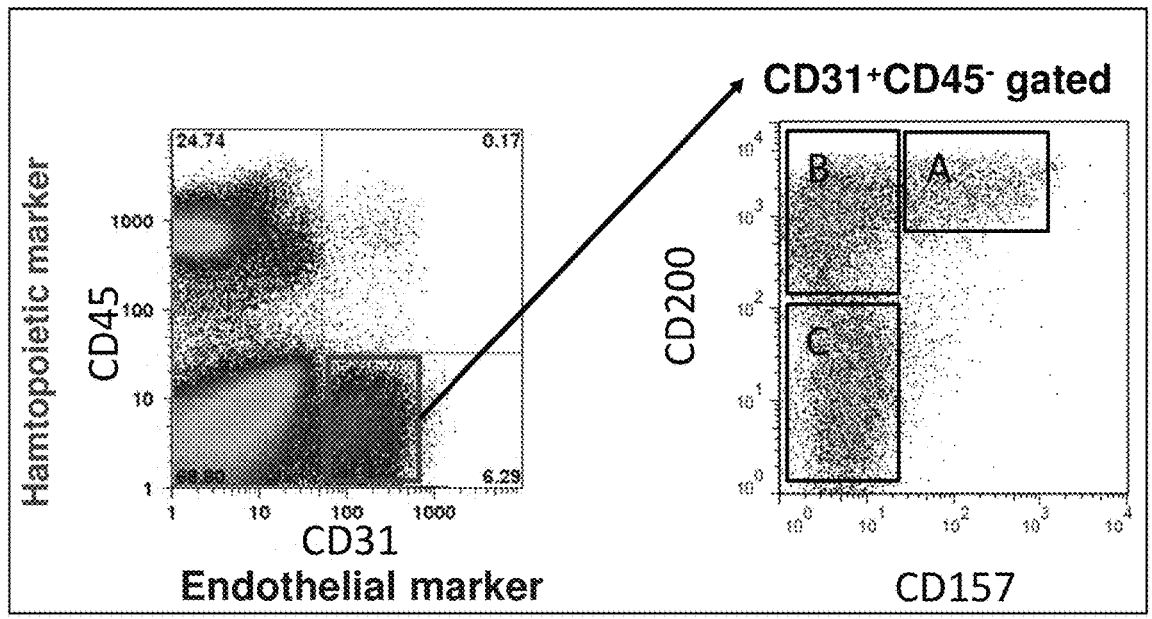
FIG. 1A
FIG. 1B
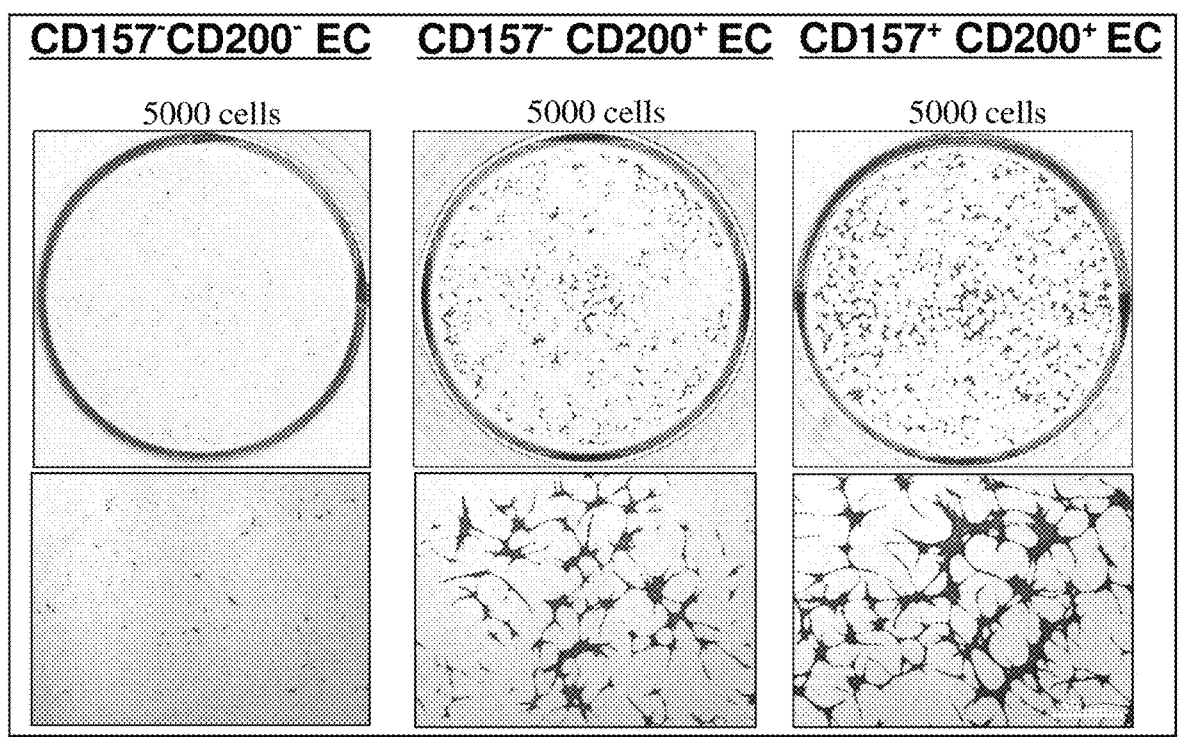
Fig. 2

EGFP CD31 nuclei

Fig. 5
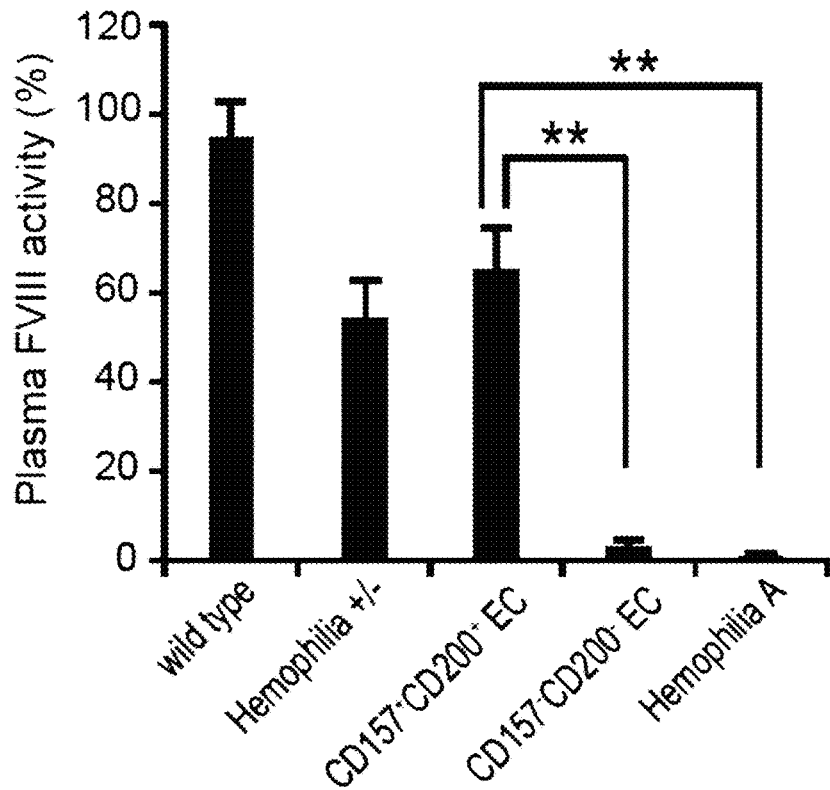
FIG. 6A
FIG. 6B
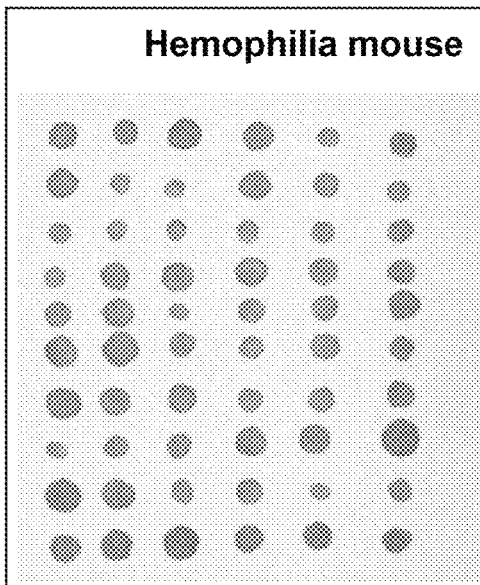
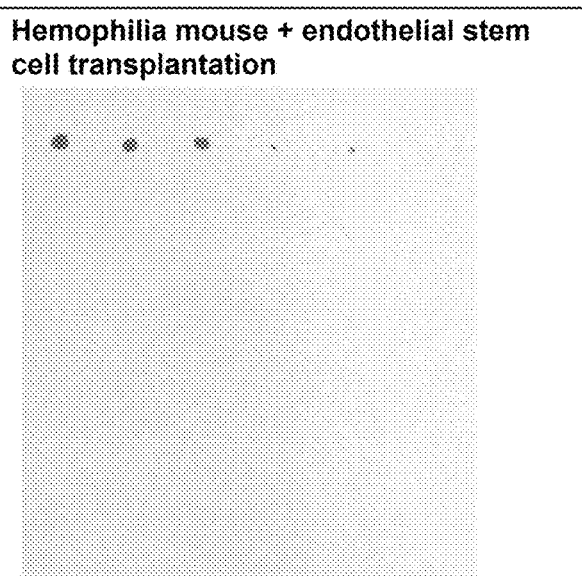

FIG. 7A
FIG.7B
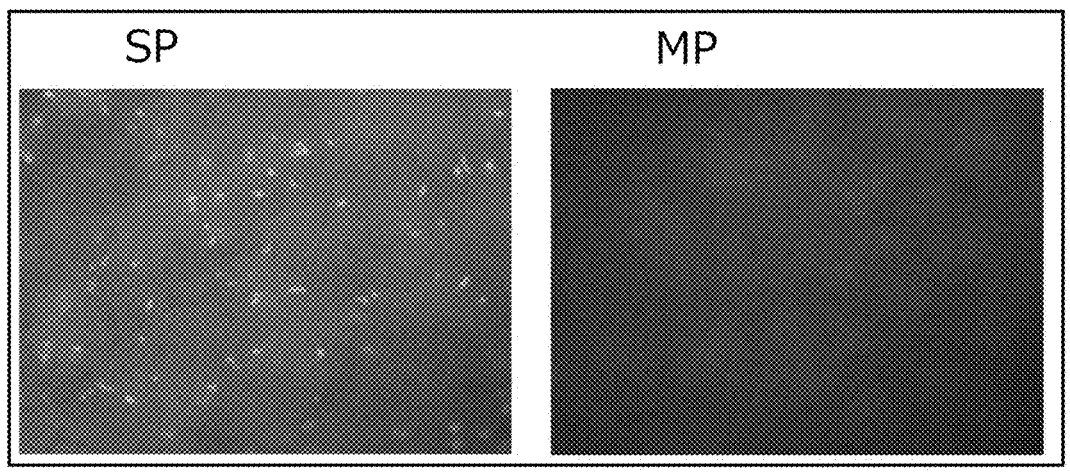
Fig. 8
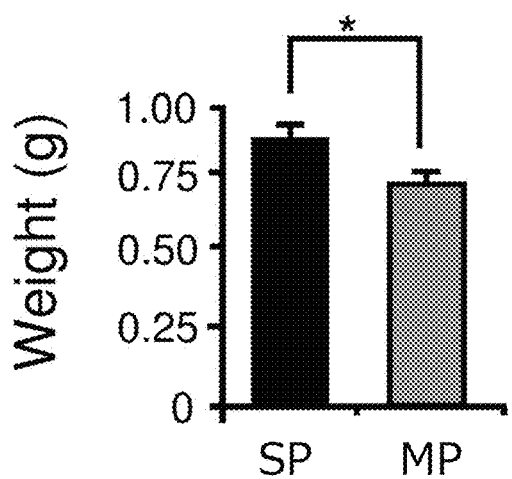
Fig. 9A
Fig. 9B
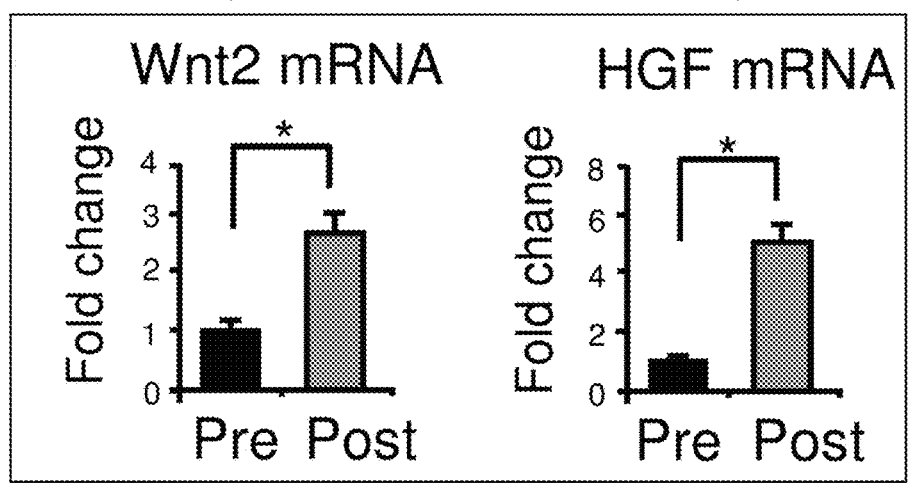

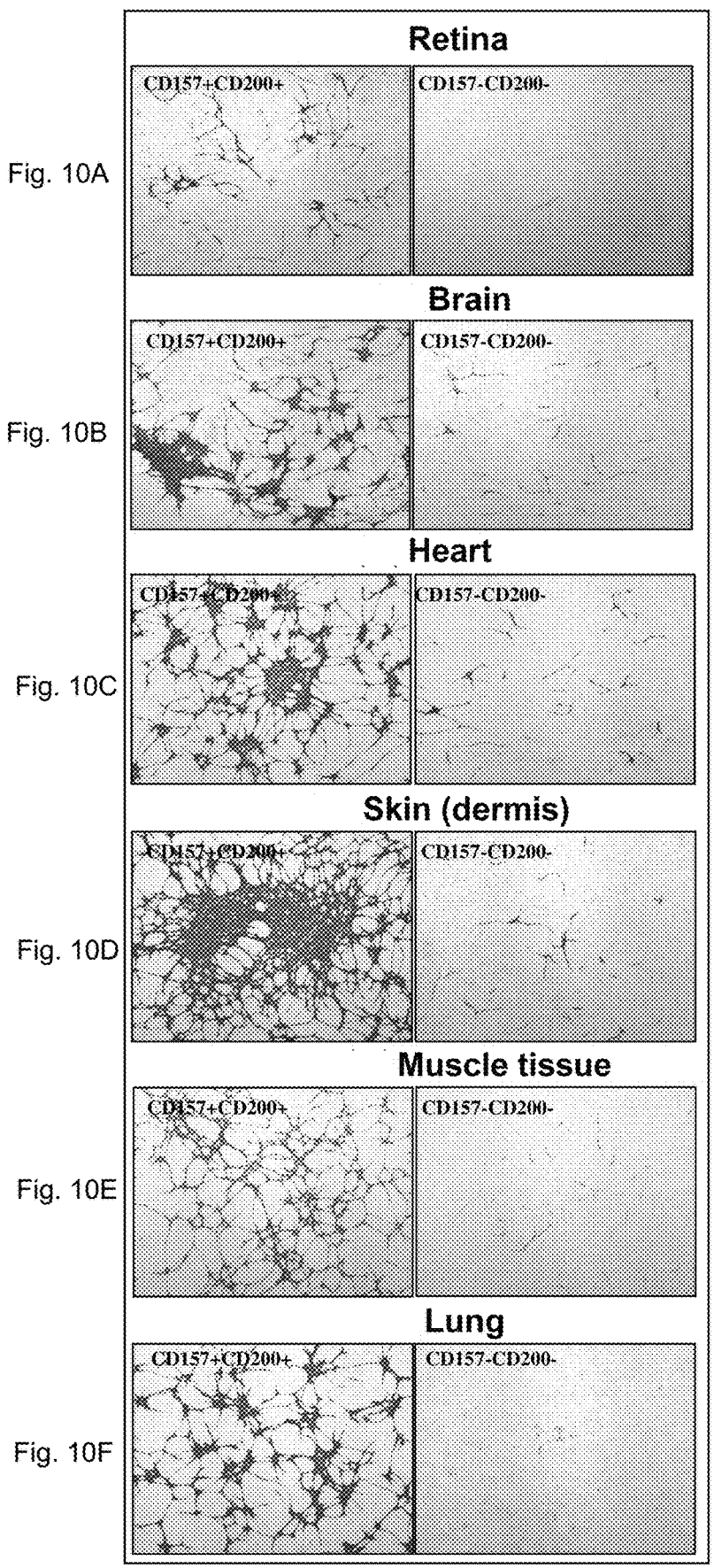

Fig. 11
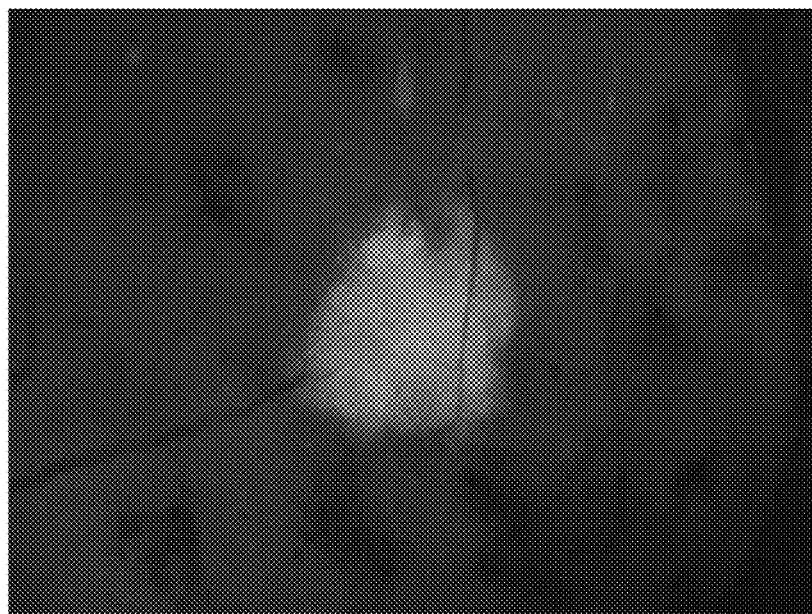
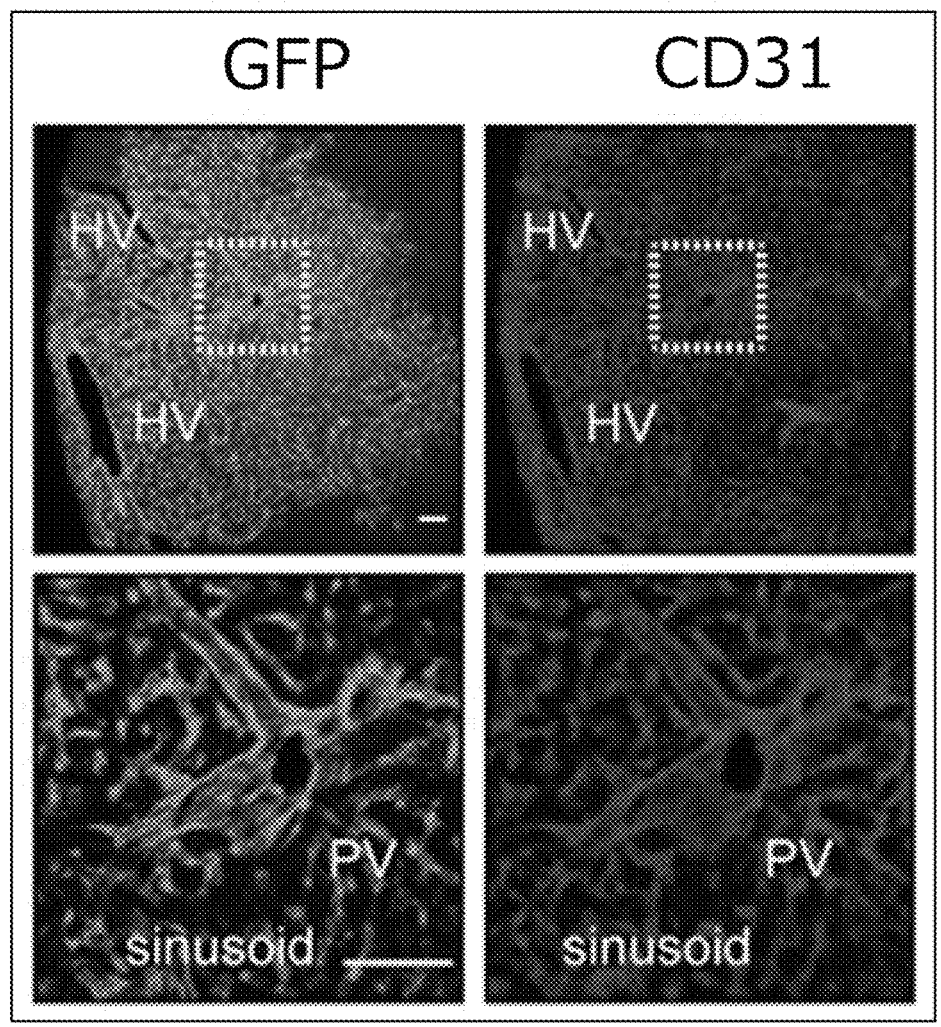
Fig. 12A                Fig. 12B

Fig. 17A
Fig. 17B
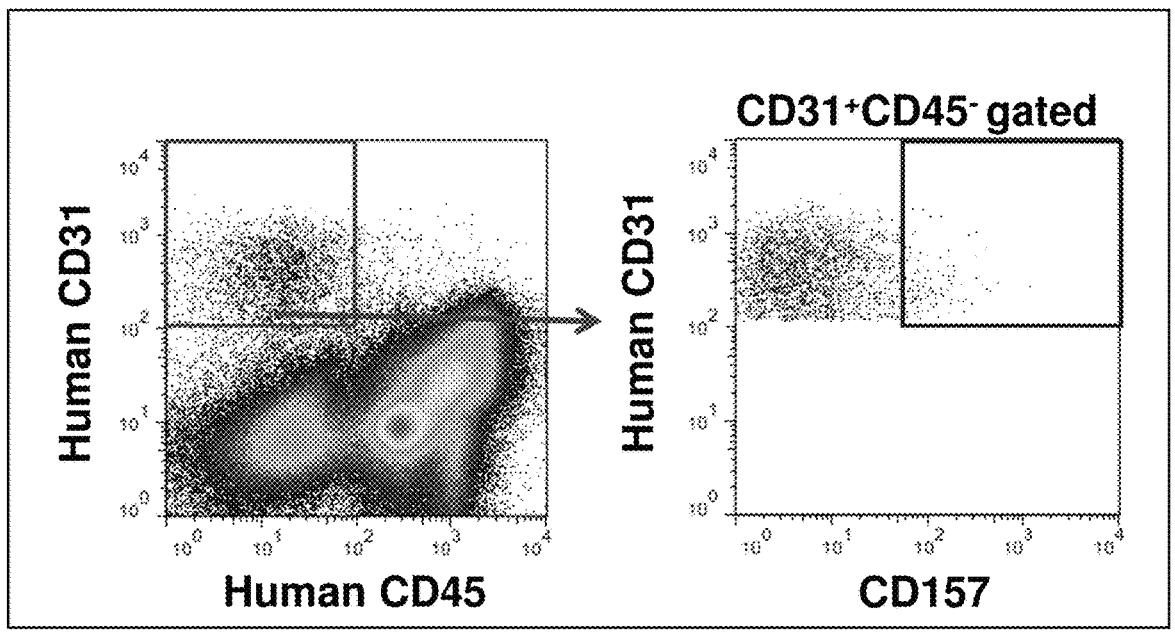
Fig. 18
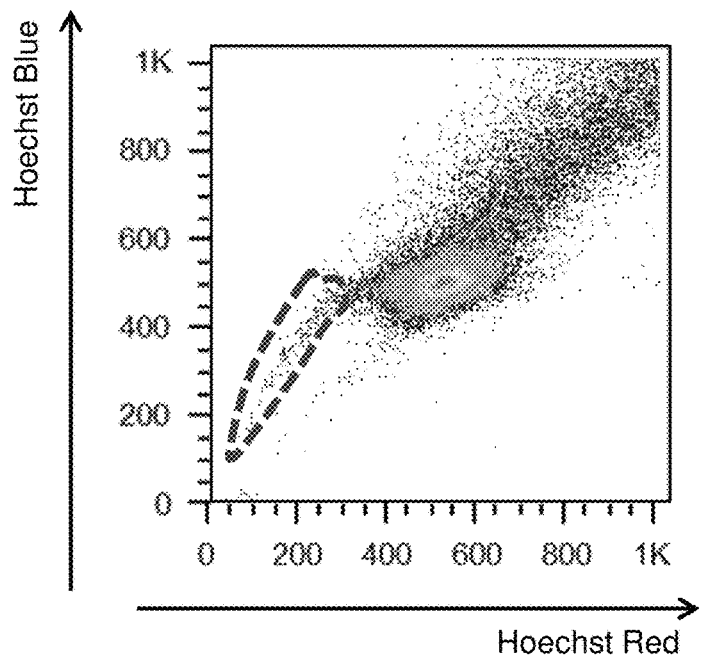

SEQUENCE LISTING

```
Sequence total quantity: 6
SEQ ID NO: 1            moltype = DNA  length = 20
FEATURE                 Location/Qualifiers
misc_feature            1..20
                        note = Primer
source                  1..20
                        mol_type = other DNA
                        organism = synthetic construct
SEQUENCE: 1
aaggacagca aaggcacctt                                                    20

SEQ ID NO: 2            moltype = DNA  length = 20
FEATURE                 Location/Qualifiers
misc_feature            1..20
                        note = Primer
source                  1..20
                        mol_type = other DNA
                        organism = synthetic construct
SEQUENCE: 2
gagccactca caccatgaca                                                    20

SEQ ID NO: 3            moltype = DNA  length = 20
FEATURE                 Location/Qualifiers
misc_feature            1..20
                        note = Primer
source                  1..20
                        mol_type = other DNA
                        organism = synthetic construct
SEQUENCE: 3
accctggtgt ttcacaagca                                                    20

SEQ ID NO: 4            moltype = DNA  length = 20
FEATURE                 Location/Qualifiers
misc_feature            1..20
                        note = Primer
source                  1..20
                        mol_type = other DNA
                        organism = synthetic construct
SEQUENCE: 4
caagaacttg tgccggtgtg                                                    20

SEQ ID NO: 5            moltype = DNA  length = 20
FEATURE                 Location/Qualifiers
misc_feature            1..20
                        note = Primer
source                  1..20
```

```
                        mol_type = other DNA
                        organism = synthetic construct
SEQUENCE: 5
aactttggca ttgtggaagg                                                    20

SEQ ID NO: 6            moltype = DNA  length = 20
FEATURE                 Location/Qualifiers
misc_feature            1..20
                        note = Primer
source                  1..20
                        mol_type = other DNA
                        organism = synthetic construct
SEQUENCE: 6
ggatgcaggg atgatgttct                                                    20
```

CELL POPULATIONS OF CD31-POSITIVE, CD45-NEGATIVE, CD200-POSITIVE MAMMALIAN CELLS AND USE THEREOF

CROSS REFERENCE TO RELATED APPLICATIONS

This application is a Divisional application of U.S. patent application Ser. No. 16/763,938, filed on May 13, 2020, which is a U.S. National Phase Application of PCT International Application Number PCT/JP2018/042255, filed on Nov. 15, 2018, designating the United States of America and published in the Japanese language, which is an International Application of and claims the benefit of priority to Japanese Patent Application No. 2017-221955, filed on Nov. 17, 2017. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SeqList-IWAT007-009D1, created Jan. 26, 2024, which is approximately 8,587 bytes in size. The information in the electronic format of the Sequence Listing is expressly incorporated herein by reference in its entirety.

TECHNICAL FIELD

The present invention relates to a cell population of CD31-positive, CD45-negative, CD200-positive mammalian cells, and a medicament comprising the cell population as an active ingredient.

BACKGROUND ART

Hematopoietic stem cells residing in the bone marrow are known to possess the ability to divide themselves with maintenance of the undifferentiated state (self-renewal capacity) and the ability to differentiate into mature hemocytes, such as erythrocytes and leukocytes, and progenitor cells for platelets. Due to these abilities, hematopoietic stem cells maintain myelopoiesis over a long period of time. On the other hand, vascular endothelial cells forming the vascular lumen were widely believed to serve as slowly dividing mature cells after generated during the fetal period and continue to maintain the blood vessels throughout their life. In other words, stem cells supporting the blood vessels over a long period of time were not considered to reside in the blood vascular system.

The inventors assumed that some sort of vascular endothelial stem cell-like cells capable of producing a large number of vascular endothelial cells may reside in preexisting blood vessels, and investigated whether heterogeneity exists in vascular endothelial cells using the Hoechst method, a known isolation method for tissue-resident stem cells. The Hoechst method utilizes the fact that tissue-resident stem cells have a higher ability to efflux drugs (foreign bodies) than differentiated cells. Analysis of incorporation of Hoechst 33342 DNA dye can be used to identify cells with a high ability to efflux Hoechst 33342, some of which would manifest stem cell capacity. The inventors examined preexisting blood vessels in the muscles of the lower extremities of mice as experimental materials, and discovered that cells with a high ability to efflux Hoechst 33342, termed side population cells (hereinafter called the "SP cell population"), reside in the vascular endothelial cells, accounting for about 1% of the total vascular endothelial cells. A comparison of the SP cell population with the main population cells, which are incapable of effluxing Hoechst (hereinafter the cells are called the "MP cell population"), revealed that cells capable of producing a large number of vascular endothelial cells from a single cell make up about 10% of the SP cell population, but such cells are almost absent from the MP cell population. When these vascular endothelial cells of each of the SP and MP cell populations were transplanted into the thigh muscles of ischemia mice induced by femoral artery ligation, the SP cell population was capable of differentiating into vascular endothelial cells to form complete blood vessels, but the MP cell population almost did not have such a capability. The transplanted SP cell population served as a source of the MP cell population and contributed to blood vessel formation, indicating that vascular endothelial stem cell-like cells reside in the SP cell population and have a capability for regenerating new blood vessels (non-patent literature 1). As previously reported, vascular endothelial progenitor cells reside in the bone marrow, and have been used for revascularization therapy. These cells can transiently differentiate into vascular endothelial cell-like cells, but are incapable of serving continuously as vascular endothelial cells. The inventors have confirmed that the vascular endothelial stem cell-like cells found in the muscle-resident vascular endothelial cells are not bone marrow-derived cells (non-patent literature 1).

CITATION LIST

Non-Patent Literature

Non-patent literature 1: Naito H, Kidoya H, Sakimoto S, Wakabayashi T, Takakura N. Identification and characterization of a resident vascular stem/progenitor cell population in preexisting blood vessels. EMBO J. 2012 Feb. 15; 31 (4): 842-55.

SUMMARY OF INVENTION

Technical Problem

An object invention is to identify vascular endothelial stem cells and a vascular endothelial stem cell population by cell surface markers and to provide a medicament comprising the vascular endothelial stem cells or the vascular endothelial stem cell population as an active ingredient.

Solution to Problem

The present invention was made to solve the above problems and includes the following.

[1] A cell population substantially consisting of mammalian cells that are positive for cell surface markers CD31 and CD200 and negative for CD45.

[2] A cell population substantially consisting of mammalian cells that are positive for cell surface markers CD31, CD157 and CD200 and negative for CD45.

[3] The cell population according to the above [1] or [2], which comprises vascular endothelial stem cells.

[4] The cell population according to the above [1] or [2], wherein the mammalian cells comprise vascular endothelial stem cells expressing a transgene.

[5] The cell population according to any one of the above [1] to [4], wherein the mammal is a human.

[6] A mammalian vascular endothelial stem cell that is positive for the cell surface marker CD31, positive for at least one of CD157 and CD200, and negative for CD45.

[7] The vascular endothelial stem cell according to the above [6], which expresses a transgene.

[8] The vascular endothelial stem cell according to the above [6] or [7], wherein the mammal is a human.

[9] A medicament comprising the cell population according to any one of the above [1] to [5] or the vascular endothelial stem cell according to any one of the above [6] to [8] as an active ingredient.

[10] The medicament according to the above [9], wherein the medicament is for vascular regeneration, improvement of ischemia, improvement of undernutrition, treatment of vascular malformation, improvement of blood flow impairment caused by vascular malformation, promotion of organ regeneration, or prevention and/or treatment of a disease caused by an abnormality of a molecule secreted from vascular endothelial cells.

[11] The medicament according to the above [10], wherein the disease caused by an abnormality of a molecule secreted from vascular endothelial cells is hemophilia A, hemophilia B, von Willebrand disease, hypertension, impaired glucose tolerance, lipid metabolism disorder, metabolic syndrome or osteoporosis.

[12] A medicament for preventing and/or treating a disease, the medicament comprising the cell population according to the above [4] or the vascular endothelial stem cell according to the above [7] as an active ingredient, wherein the disease is improved by a transgene product produced from the cells.

[13] The medicament according to the above [12], wherein the disease improved by the transgene product is hemophilia A, hemophilia B, von Willebrand disease, a cancer, age-related macular degeneration, an autoimmune disease, rheumatism, dementia, diabetes mellitus, hypertension, diabetic nephropathy, osteoporosis, obesity or an infection.

[14] A method for evaluating vascular toxicity of a test substance, the method comprising the steps of:
(1) culturing the cell population according to any one of the above [1] to [5] in a culture medium containing the test substance and in a culture medium free of the test substance,
(2) measuring cell proliferation levels after culturing, and
(3) comparing the cell proliferation level of the cell population cultured in the culture medium containing the test substance with the cell proliferation level of the cell population cultured in the culture medium free of the test substance.

Advantageous Effects of Invention

The present invention provides a vascular endothelial stem cell population and vascular endothelial stem cells. The cell population and the vascular endothelial stem cells of the present invention can be used to provide a medicament for vascular regeneration, of ischemia, improvement improvement of undernutrition, treatment of vascular malformation, improvement of blood flow impairment caused by vascular malformation, promotion of organ regeneration, or treatment of a disease caused by an abnormality of a molecule secreted from vascular endothelial cells. Also, vascular endothelial stem cells modified to express a transgene can be used to provide a medicament for treating a disease improved by a product of the transgene.

BRIEF DESCRIPTION OF DRAWINGS

FIGS. 1A and 1B show the results of flow cytometric analysis of immunofluorescence stained mouse liver cells prepared by digestion and dissociation of mouse liver. FIG. 1A shows the results of flow cytometric analysis of the mouse liver cells stained with anti-CD31 and anti-CD45 antibodies. FIG. 1B shows the results of flow cytometric analysis of the mouse liver cells in the boxed region ($CD31^+$ $CD45^-$ cells) in FIG. 1A stained with anti-CD157 and anti-CD200 antibodies.

FIG. 2 shows the results of colony-forming assays of the cells of fraction A ($CD157^+CD200^+$), fraction B ($CD157^-CD200^+$) and fraction C ($CD157^-CD200^-$) as shown in FIG. 1B.

FIG. 5 shows the measurement results of plasma coagulation factor VIII activities in wild-type mice, coagulation factor VIII gene-heterozygous deficient mice, hemophilia model mice (coagulation factor VIII gene-deficient mice), hemophilia A model mice transplanted with $CD157^+$ $CD200^+$ vascular endothelial cells and hemophilia A model mice transplanted with CD157-CD200– vascular endothelial cells.

FIGS. 6A and 6B show the bleeding time in hemophilia A model mice transplanted with $CD157^+CD200^+$ vascular endothelial cells and hemophilia A model mice with no cell transplantation.

FIGS. 7A and 7B show fluorescence microscopic images of the livers of 70% partially hepatectomized mice 7 days after transplantation of SP or MP population cells into the livers. FIG. 7A shows a fluorescence microscopic image of the liver transplanted with SP population cells, and FIG. 7B shows a fluorescence microscopic image of the liver transplanted with the MP population cells.

FIG. 8 shows the measurement results of the weight of the livers of 70% partially hepatectomized mice 7 days after transplantation of SP or MP population cells into the livers.

FIGS. 9A and 9B show the mRNA expression levels of Wnt2 and HGF in SP population cells before transplantation (Pre) and in GFP-positive vascular endothelial cells ($GFP^+$ $CD31^+CD45^-$ cells) prepared from the livers of 70% partially hepatectomized mice 7 days after transplantation of SP population cells into the livers (Post). FIGS. 9A and 9B show the mRNA expression levels of Wnt2 and HGF, respectively.

FIGS. 10A to 10F show the results of colony-forming assays of $CD31^+CD45^-CD157^+CD200^+$ cells collected by immunofluorescence staining performed on cells prepared by digestion and dissociation of the retina, brain, heart, skin, muscle tissue and lung of mice.

FIG. 11 shows a fluorescence stereomicroscopic image of the liver of a recipient mouse 1 month after transplantation of a single CD157⁺CD200⁺ vascular endothelial cell prepared from the livers of C57BL/6-Tg (CAG-EGFP) mice into the liver of the recipient mouse.

FIGS. 12A and 12B show confocal microscopic images of the immunofluorescence stained livers of the recipient mice of FIG. 11. FIG. 12A shows sections stained with an anti-GFP antibody, and FIG. 12B shows sections stained with an anti-CD31 antibody. Higher magnifications of areas (around the sinusoid) indicated by the dotted boxes in the top panels are shown in the bottom panels.

FIG. 14A shows the results of flow cytometric analysis of the human liver cells stained with anti-CD31 and anti-CD45 antibodies. FIG. 14B shows the results of flow cytometric analysis of the human liver cells in the boxed region (CD31⁺CD45⁻ cells) in FIG. 14A, stained with anti-CD157 and anti-CD200 antibodies.

FIG. 16A shows the results of flow cytometric analysis of the human kidney cells stained with anti-CD31 and anti-CD45 antibodies. FIG. 16B shows the results of flow cytometric analysis of the human kidney cells in the boxed region (CD31⁺CD45⁻ cells) in FIG. 16A stained with anti-CD157 and anti-CD31 antibodies.

FIGS. 17A and 17B show the results of flow cytometric analysis of immunofluorescence stained human placenta cells prepared by digestion and dissociation of human placenta tissue. FIG. 17A shows the results of flow cytometric analysis of the human placenta cells stained with anti-CD31 and anti-CD45 antibodies. FIG. 17B shows the results of flow cytometric analysis of the human placenta cells in the boxed region (CD31⁺CD45⁻ cells) in FIG. 17A stained with anti-CD157 and anti-CD31 antibodies.

FIG. 18 shows the results of Hoechst analysis with a flow cytometer performed on CD31⁺CD45⁻ cells collected by immunofluorescence staining and Hoechst staining of human skin cells prepared by digestion and dissociation of human skin tissue.

DESCRIPTION OF EMBODIMENTS

Figure 3:
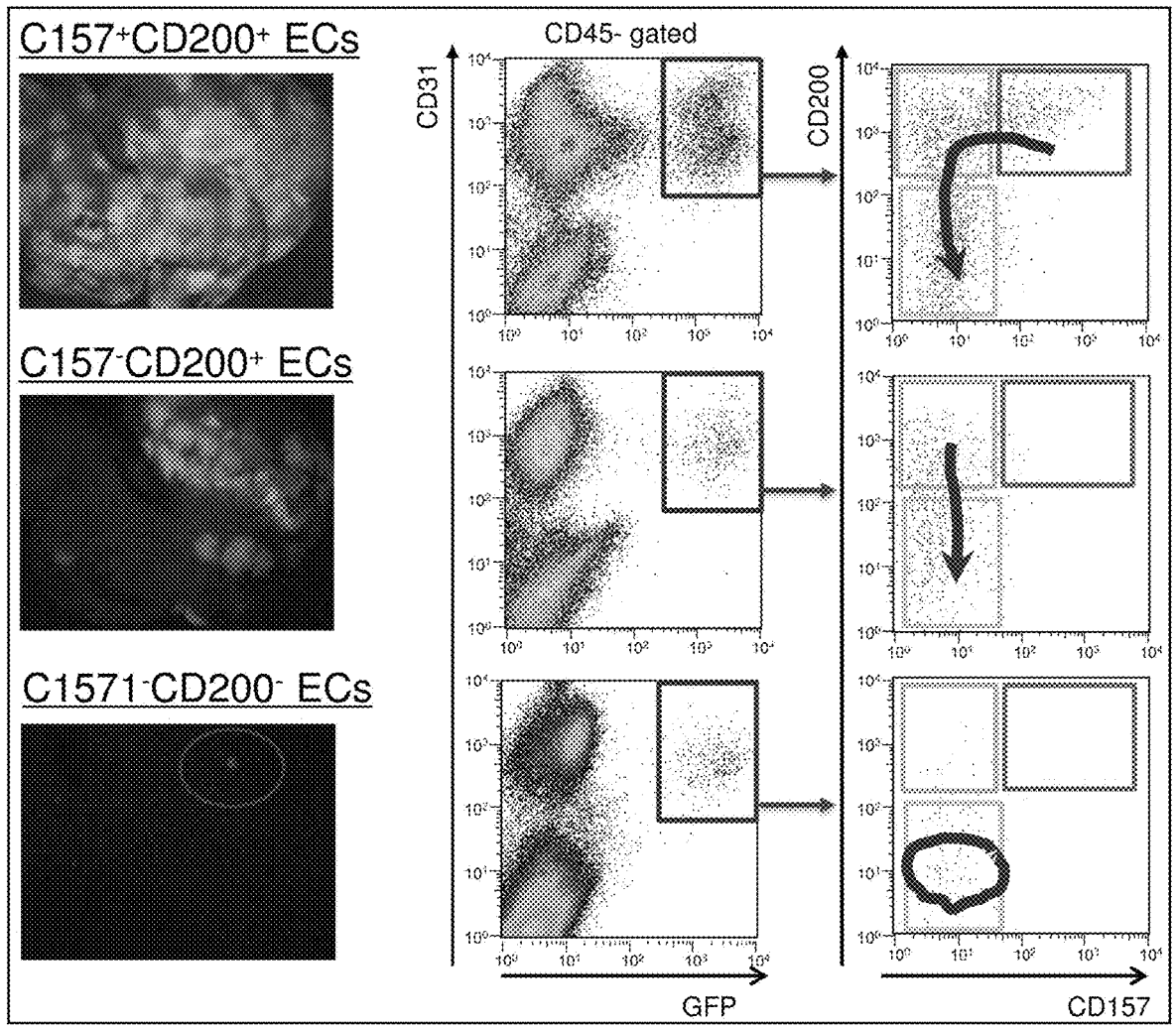
FIG. 3 shows microscopic images and plots for investigating vascular regeneration in livers after transplantation of the cells of fraction A ($CD157^+CD200^+$), fraction B ($CD157^-CD200^+$) and fraction C ($CD157^-CD200^-$) as shown in FIG. 1B into the livers of liver vascular injury model mice.

Vascular Endothelial Stem Cells and a Cell Population Comprising Vascular Endothelial Stem Cells The inventors found that cells with a high ability to efflux drugs (foreign bodies) (the SP cell population) reside in vascular endothelial cells isolated from the blood vessels of muscle tissue, accounting for about 1% of the total vascular endothelial cells. The inventors also found that the SP cell population contains vascular endothelial stem cell-like cells. The inventors, however, found that vascular endothelial stem cell like-cells are almost absent from the remaining majority of vascular endothelial cells, which have a low ability to efflux drugs (foreign bodies) (the MP cell population) (non-patent literature 1). The inventors then confirmed that vascular endothelial cells isolated from the blood vessels of the liver can also be divided into the SP cell population fraction, which has a high ability to efflux drugs (foreign bodies), and the MP cell population fraction, which has a low ability to efflux drugs (foreign bodies). The inventors also confirmed that vascular endothelial stem cell-like cells account for about 10% of the SP cell population, but are almost absent from the MP cell population. As described herein, the inventors prepared SP and MP cell populations from the liver, and comprehensively analyzed genes expressed higher in the SP cell population than in the MP cell population to identify marker molecules capable of efficiently distinguishing vascular endothelial stem cell-like cells from other vascular endothelial cells. From more than 100 genes highly expressed in the SP cell population, the inventors successfully discovered cell surface markers capable of identifying vascular endothelial stem cell-like cells (hereinafter called "vascular endothelial stem cells").

The present invention provides a cell population comprising mammalian vascular endothelial stem cells. The term "vascular endothelial stem cells" as used herein refers to cells with the ability to divide themselves with maintenance of the undifferentiated state (self-renewal capacity) and the ability to differentiate into vascular endothelial cells. A first cell population according to the present invention is a cell population substantially consisting of mammalian cells that are positive for cell surface markers CD31 and CD200 and negative for CD45. The first cell population of the present invention may contain impurity cells (cells other than CD31⁺/CD200⁺/CD45⁻ cells) that are too small in number to be removed from the cell population by a usual procedure.

CD31, also called PECAM-1, is a single-chain membrane glycoprotein of 140 kDa molecular weight and a member of the immunoglobulin superfamily. CD31 is used as a cell surface marker for endothelial cells. CD45, also called leukocyte common antigen (LCA), is a single-chain transmembrane protein and has at least five isoforms. Cells with CD31-positive and CD45-negative cell surface markers in the present invention are defined as vascular endothelial cells. Therefore, the term "CD31-positive, CD45-negative cells" as used herein is interchangeable with the term "vascular endothelial cells."

CD200 is a highly conserved membrane glycoprotein that belongs to the immunoglobulin superfamily containing two immunoglobulin-like domains (V, C), a single transmembrane and a short cytoplasmic domain. Diverse cell types express CD200 on the cell surface, including thymocytes, B cells, activated T and B cells, dendritic cells, neurons and endothelial cells. The inventors found that vascular endothelial stem cells reside in CD200-positive vascular endothelial cells (CD31-positive, CD45-negative cells). The percentage of vascular endothelial stem cells contained in the first cell population of the present invention may be about 2%, about 3%, about 4%, about 5%, about 6%, about 7%, about 8%, about 9%, or about 10%. The percentage of vascular endothelial stem cells contained in the first cell population of the present invention may be from 1 to 3%, from 2 to 4%, from 3 to 5%, from 4 to 6%, from 5 to 7%, from 6 to 8%, from 7 to 9%, or from 8 to 10%.

A second cell population according to the present invention is a cell population substantially consisting of mammalian cells that are positive for cell surface markers CD31, CD157 and CD200 and negative for CD45. The second cell population of the present invention may contain impurity cells (cells other than CD31⁺/CD157⁺/CD200⁺/CD45⁻ cells) that are too small in number to be removed from the cell population by a usual procedure.

CD157 is a glycosyl-phosphatidylinositol-anchored membrane protein, and is expressed in monocytes, neutrophils and all the lymphoid and myeloid progenitor cells. The inventors found that CD200-positive vascular endothelial cells (the first cell population) contain two cell sub-populations: a CD157-positive sub-population and a CD157-negative sub-population. The CD157-positive cell sub-population contains a large number of vascular endothelial stem cells, whereas the CD157-negative cell sub-population contains a large number of vascular endothelial progenitor cells, which are at a more differentiated stage than vascular endothelial stem cells. The percentage of vascular endothelial stem cells contained in the second cell population of the present invention may be about 20%, about 30%, about 40%, about 50%, about 60%, about 70%, about 80%, about 90%, or about 95%. The percentage of vascular endothelial stem cells contained in the second cell population of the present invention may be from 20 to 40%, from 30 to 50%, from 40 to 60%, from 50 to 70%, from 60 to 80%, from 70 to 90%, from 80 to 95%, or from 90 to 99%.

The cell population of the present invention is a mammalian cell population. The mammal is not limited to a particular species, and examples thereof include humans, monkeys, cow, pigs, dogs, mice, rats, rabbits, etc. When the cell population of the present invention is a human cell population, the cell population can be safely transplanted into humans.

The present invention may provide vascular endothelial stem cells that do not form a cell population. In other words, the present invention includes individual vascular endothelial stem cells. The vascular endothelial stem cells of the present invention may be mammalian vascular endothelial stem cells that are positive for cell surface markers CD31 and CD200 and negative for CD45, or may be mammalian vascular endothelial stem cells that are positive for cell surface markers CD31, CD157 and CD200 and negative for CD45. The mammal is not limited to a particular species, and examples thereof include humans, monkeys, cow, pigs, dogs, mice, rabbits, rats, etc. When the vascular endothelial stem cells of the present invention are human vascular endothelial stem cells, the cells can be safely transplanted into humans.

The cell population and the vascular endothelial stem cells of the present invention can be prepared from any organ. The cell population and the vascular endothelial stem cells have been demonstrated to be able to be prepared from, for example, liver, retina, brain, heart, skin, muscles (skeletal muscles), lung, kidney, placenta, etc. (see Examples 1, 4, 6 and 7). The cell population of the present invention may be prepared by any preparation method, but may be prepared by, for example, digesting and dissociating a harvested organ in a commercially available cell dissociation reagent to prepare a cell suspension, staining the cell suspension with anti-CD31, anti-CD45 and anti-CD200 antibodies, and collecting $CD31^+CD45^-CD200^+$ cells (first cell population) by flow cytometry techniques. Alternatively, the cell suspension may be stained with anti-CD31, anti-CD45, anti-CD157 and anti-CD200 antibodies, and $CD31^+CD45^-CD157^+CD200^+$ cells (second cell population) may be collected by flow cytometry techniques (see Example 1).

The vascular endothelial stem cells may be vascular endothelial stem cells expressing a transgene. The present invention thus includes vascular endothelial stem cells expressing a transgene, and a cell population comprising vascular endothelial stem cells expressing a transgene. The transgene is not limited to a particular gene, and may be a gene encoding a gene product that exhibits an advantageous effect on a living body. The transgene may be a gene encoding a gene product to be extracellularly secreted. Examples of the transgene include a gene encoding an antibody that recognizes a specific antigen, a gene encoding a cytokine, a gene encoding a nucleic acid that hybridizes to a specific nucleic acid sequence, etc.

The vascular endothelial stem cells expressing a transgene can be produced using known genetic modification techniques. For example, the vascular endothelial stem cells expressing a transgene can be produced by inserting a desired gene into an expression vector, and transfecting $CD31^+CD45^-CD200^+$ cells or $CD31^+CD45^-CD157^+CD200^+$ cells prepared as described above with the expression vector.

Medicaments

The present invention provides a medicament comprising the cell population of the present invention as an active ingredient. The inventors have confirmed that, when the cell population of the present invention is transplanted into the livers of liver vascular injury model mice, the vascular endothelial stem cells contained in the cell population regenerate blood vessels (see Example 1). The present invention also provides a medicament comprising the vascular endothelial stem cells of the present invention as an active ingredient. The inventors have confirmed that, when a single vascular endothelial stem cell of the present invention is transplanted into the livers of recipient mice, the single vascular endothelial stem cell resides in the livers and expands to produce vascular endothelial cells to form blood vessels, and maintains itself over a long period of time (see Example 5).

The medicament of the present invention is suitable for vascular regeneration. The medicament of the present invention induces vascular regeneration and can thus be used for improvement of ischemia and undernutrition caused by reduction of vascular function. The medicament of the present invention is therefore effective for treatment of ischemic diseases, such as cerebral infarction, myocardial infarction and Buerger disease. These ischemic diseases may be those associated with arterial diseases, such as arteriosclerosis, thrombosis and arteritis, or may be those associated with lifestyle-related such diseases, as hyperlipemia, diabetes mellitus, hypertension, gout and aging. The medicament of the present invention is suitable for treatment of vascular malformation or treatment of blood flow impairment caused by vascular malformation. The vascular malformation may be due to, for example, arteriovenous fistula, moyamoya disease, etc. The medicament of the present invention can also be used for wound healing.

The medicament of the present invention can also be used for promotion of organ regeneration. The inventors have confirmed that, when the cell population of the present invention is transplanted into the livers of 70% partially hepatectomized mice, liver regeneration is promoted (see Example 3). The organ to be subjected to promotion of regeneration is not limited to a particular organ, and may be any organ whose blood vessels can be regenerated by the medicament of the present invention. As previously described, organ-specific cells (including stem cells) in every organ are supported by humoral factors and adhesion factors from vascular endothelial cells for prolonged survival and proliferation. Regeneration of organ blood vessels, therefore, leads to promotion of organ regeneration. In a similar manner, the medicament of the present invention treats a disease that can be improved through organ regeneration. For example, cirrhosis, hepatic fibrosis, hepatitis, fatty liver, hepatic failure, or the like is prevented or treated by promotion of liver regeneration. The same applies to other organs.

The medicament of the present invention can also be used to treat a disease caused by an abnormality of a molecule secreted from vascular endothelial cells. For example, when the medicament of the present invention comprising vascular endothelial stem cells having a normal gene is applied to a patient with a disease caused by absence of or reduction in secretion of a molecule from vascular endothelial cells due to an abnormality of a gene, blood vessels are regenerated and the required amount of the molecule starts to be secreted from the vascular endothelial cells of the regenerated blood vessels, and in turn the disease can be cured efficiently. The inventors have confirmed that, when the cell population of the present invention prepared from the livers of mice having a normal coagulation factor VIII gene is administered to the livers of hemophilia A model mice, the time from the onset of bleeding till the stoppage f bleeding is significantly shortened (see Example 2).

The disease caused by an abnormality of a molecule secreted from vascular endothelial cells may be, for example, hemophilia A, hemophilia B, von Willebrand disease, hypertension, impaired glucose tolerance, lipid metabolism disorder, metabolic syndrome, osteoporosis, etc. Table 1 shows molecules secreted from vascular endothelial cells corresponding to these diseases.

TABLE 1

| Disease names | Factors secreted from vascular endothelial cells |
|---|---|
| Hemophilia A | Coagulation factor VIII |
| Hemophilia B | Coagulation factor IX |
| Von Willebrand disease | Von Willebrand factor |
| Hypertension | Nitrogen monoxide etc. |
| Impaired glucose tolerance | Nitrogen monoxide etc. |
| Lipid metabolism disorder | Nitrogen monoxide etc. |
| Metabolic syndrome | Apelin etc. |
| Osteoporosis | Notch ligand, netrin, endothelin-1, etc. |

The cell population or the vascular endothelial stem cells of the present invention contained in the medicament of the present invention are selected so as to be appropriate for an organ to be subjected to vascular regeneration. As well known in the art, an organ is derived from one of three germ layers (endoderm, mesoderm and ectoderm) formed during the embryonic developmental stage, and the cell population of the present invention appropriate for an organ to be subjected to vascular regeneration may be a cell population prepared according to the present invention from an organ originating from the same germ layer as the organ to be treated. Examples of the organs originating from the endoderm include stomach, intestines, lung, liver, pancreas, etc. Examples of the organs originating from the mesoderm include muscles, bones, blood vessels, heart, kidney, spleen, testis, uterus, etc. Examples of the organs originating from the ectoderm include brain, nerves, skin, crystalline lens, etc. Preferred is a cell population prepared according to the present invention from the same type of organ as the organ to be subjected to vascular regeneration.

The present invention provides a medicament comprising vascular endothelial stem cells expressing a transgene or a cell population comprising vascular endothelial stem cells expressing a transgene as an active ingredient. When vascular endothelial stem cells expressing a transgene are transplanted into an organ or tissue, the vascular endothelial stem cells reside in the blood vessels of the organ or tissue and serve as a source of vascular endothelial cells, and at the same time the cells continuously and persistently express the transgene and secrete a product of the transgene into the blood, and the secreted transgene product is delivered to the diseased site via the blood flow. In this manner, the vascular endothelial stem cells expressing a transgene are appropriately used for prevention and/or treatment of a disease improved by the effects of a product of the transgene.

The medicament comprising vascular endothelial stem cells expressing a transgene or a cell population comprising vascular endothelial stem cells expressing a transgene as an active ingredient can be used to treat any disease that is effectively treated with a product of the transgene. Specific examples of the medicament include a medicament for treating hemophilia comprising vascular endothelial stem cells transduced with a gene encoding coagulation factor VIII, a medicament for treating hemophilia comprising vascular endothelial stem cells transduced with a gene encoding coagulation factor IX, a medicament for treating hemophilia comprising vascular endothelial stem cells transduced with a gene encoding an anti-coagulation factor VIII antibody, a medicament for bleeding disorders (von Willebrand disease etc.) comprising vascular endothelial stem cells transduced with a gene encoding von Willebrand factor, a medicament for treating angioproliferative diseases (cancers, age-related macular degeneration, etc.) comprising vascular endothelial stem cells transduced with a gene encoding an anti-VEGF antibody or an anti-VEGF receptor antibody, a medicament for treating autoimmune diseases (rheumatism etc.) comprising vascular endothelial stem cells transduced with a gene encoding an anti-inflammatory cytokine (IL-6 etc.) antibody, a medicament for treating dementia comprising vascular endothelial stem cells transduced with a gene encoding an anti-amyloid β antibody, a medicament for treating diabetes mellitus comprising vascular endothelial stem cells transduced with a gene encoding insulin, a medicament for treating acquired immunodeficiency syndrome (AIDS) comprising vascular endothelial stem cells transduced with a gene encoding an antisense nucleic acid of IE2 mRNA of a cytomegalovirus gene, a medicament for treating vascular permeability disorders (hypertension, diabetic nephropathy, etc.) comprising vascular endothelial stem cells transduced with a gene encoding the Tie2 agonist angiopoietin-1, a medicament for treating osteoporosis comprising vascular endothelial stem cells transduced with a gene encoding Noggin, a medicament for reducing obesity comprising vascular endothelial stem cells transduced with a gene encoding an obesity gene product (leptin etc.), a medicament for cancer vaccine therapy comprising vascular endothelial stem cells transduced with a gene encoding a cancer antigen, a medicament for preventing and treating infections comprising vascular endothelial stem cells transduced with a gene encoding a viral antigen, etc.

The medicament of the present invention for administration to a living body may be in the form of a cell suspension prepared by suspending the cell population or the vascular endothelial stem cells of the present invention in an appropriate solution that can be administered to a living body. Examples of the solution that can be administered to a living body include physiological saline, PBS (phosphate buffered saline), and other physiological salt solutions.

The cell population or the vascular endothelial stem cells typically prepared immediately prior to administration, but may be prepared at time of use from a cryopreserved cell population or cryopreserved vascular endothelial stem cells.

The medicament of the present invention in the form of a cell suspension containing the cell population or the vascular endothelial stem cells of the present invention can be directly administered to an organ to be subjected to vascular regeneration, or can be administered into a vein upstream of an organ to be subjected to vascular regeneration. The dosage will vary depending on an organ to be subjected to vascular regeneration, the age and body weight of the patient, etc. and cannot thus be definitely specified, but a suitable dosage can be determined as appropriate by a physician with consideration of the above conditions. For example, 1 cell to $1 \times 10^9$ cells per dose may be administered. The frequency of administration can be selected as appropriate from the range of once a day to once a week. The dosage and frequency of administration can be adjusted as appropriate depending on the patient.

Method for Evaluating Vascular Toxicity

The present invention provides a method for evaluating vascular toxicity using the cell population of the present invention. The method for evaluating vascular toxicity can be performed by contacting a test substance to the cell population of the present invention, and measuring the cell proliferation level. Specifically, the method comprising, for example, the following steps:

(1) culturing the cell population according to any one of the above [1] to [3] in a culture medium containing a test substance and in a culture medium free of the test substance, (2) measuring cell proliferation levels after culturing, and (3) comparing the cell proliferation level of the cell population cultured in the culture medium containing the test substance with the cell proliferation level of the cell population cultured in the culture medium free of the test substance.

The test substance is not limited to a particular substance, and examples thereof include, but are not limited to, a nucleic acid, a peptide, a protein, a non-peptide compound, a synthetic compound, a fermentation product, a cell extract, a cell culture supernatant, a plant extract, a mammalian tissue extract, a plasma, etc. The test substance may be a novel substance or a known substance. The test substance may be in the form of a salt. A salt of the test substance may be a salt with a physiologically acceptable acid or base.

The culture medium used for culture of the cell population of the present invention can be selected as appropriate from known culture mediums that can be used for culture of vascular endothelial cells. The culture method can also be selected as appropriate from known culture methods for vascular endothelial cells. The culture period is not limited to a particular period of time, and is preferably set as appropriate depending on the test substance to be evaluated.

The measurement method for the cell proliferation level is also not limited to a particular method, and can be selected as appropriate from known methods. Specific examples of the measurement method include cell counting by visual observation or with a cell counter, the crystal violet method, the MTT method, and other methods with various cell proliferation assay kits.

When the cell proliferation level of the cell population cultured in a culture medium containing a test substance is lower than the cell proliferation level of the cell population cultured in a culture medium free of the test substance, that is, when the test substance inhibits proliferation of vascular endothelial stem cells, the test substance can be determined to have vascular toxicity. For example, when the cell proliferation level of the cell population cultured in a culture medium containing a test substance is 90% or less, 80% or less, 70% or less, 60% or less, or 50% or less of the cell proliferation level of the cell population cultured in a culture medium free of the test substance, the test substance may be determined to have vascular toxicity.

Also, when the cell proliferation level of the cell population cultured in a culture medium containing a test substance is markedly higher than the cell proliferation level of the cell population cultured in a culture medium free of the test substance, that is, when the test substance excessively promotes proliferation of vascular endothelial stem cells, the test substance can be determined to have vascular toxicity. For example, when the cell proliferation level of the cell population cultured in a culture medium containing a test substance is 200% or more, 250% or more, or 300% or more of the cell proliferation level of the cell population cultured in a culture medium free of the test substance, the test substance may be determined to have vascular toxicity.

Vascular endothelial cells harvested from an adult mammal almost do not proliferate in vitro, and are thus not appropriate for use in in vitro evaluation of vascular toxicity utilizing proliferation of the cells as an indicator. On the contrary, the cell population of the present invention proliferates in vitro, and can thus be used in in vitro evaluation of vascular toxicity utilizing proliferation of the cells as an indicator. The method for evaluating vascular toxicity according to the present invention is very useful in that the vascular toxicity of a test substance can be evaluated conveniently and quickly. The method for evaluating vascular toxicity according to the present invention is especially useful when the evaluation of a toxicity to vascular endothelial cells is desired to be carried out. The method for evaluating vascular toxicity according to the present invention is also very useful in that a cell population prepared according to the present invention from a patient can be used to evaluate an effect of a test substance on the blood vessels of the patient.

The present invention also includes the following.

[A] A method for regenerating blood vessels, the method comprising the step of administering the cell population according to any one of the above [1] to [5] or the vascular endothelial stem cell according to any one of the above [6] to [8].

[B] The method according to the above [A], wherein the method improves ischemia and undernutrition.

[C] The method according to the above [A], wherein the method treats vascular malformation or blood flow impairment caused by vascular malformation.

[D] The method according to the above [A], wherein the method promotes organ regeneration.

[E] The method according to the above [A], wherein the method treats a disease caused by an abnormality of a molecule secreted from vascular endothelial cells.

[F] The method according to the above [E], wherein the disease caused by an abnormality of a molecule secreted from vascular endothelial cells is hemophilia A, hemophilia B, von Willebrand disease, hypertension, impaired glucose tolerance, lipid metabolism disorder, metabolic syndrome or osteoporosis.

[G] The cell population according to any one of the above [1] to [5] or the vascular endothelial stem cell according to any one of the above [6] to [8] for use in vascular regeneration.

[H] The cell population or vascular endothelial stem cell for use according to the above [G], wherein the cell population or vascular endothelial stem cell improves ischemia and undernutrition.

[I] The cell population or vascular endothelial stem cell for use according to the above [G], wherein the cell population or vascular endothelial stem cell treats vascular malformation or blood flow impairment caused by vascular malformation.

[J] The cell population or vascular endothelial stem cell for use according to the above [G], wherein the cell population or vascular endothelial stem cell promotes organ regeneration.

[K] The cell population or vascular endothelial stem cell for use according to the above [G], wherein the cell population or vascular endothelial stem cell treats a disease caused by an abnormality of a molecule secreted from vascular endothelial cells.

[L] The cell population or vascular endothelial stem cell for use according to the above [K], wherein the disease caused by an abnormality of a molecule secreted from vascular endothelial cells is hemophilia A, hemophilia B, von Willebrand disease, hypertension, impaired glucose tolerance, lipid metabolism disorder, metabolic syndrome or osteoporosis.

[M] Use of the cell population according to any one of the above [1] to [5] or the vascular endothelial stem cell according to any one of the above [6] to [8] for production of a medicament for vascular regeneration.

[N] The use according to the above [M], wherein the medicament for vascular regeneration improves ischemia and undernutrition.

[O] The use according to the above [M], wherein the medicament for vascular regeneration treats vascular malformation or blood flow impairment caused by vascular malformation.

[P] The use according to the above [M], wherein the medicament for vascular regeneration promotes organ regeneration.

[Q] The use according to the above [M], wherein the medicament for vascular regeneration treats a disease caused by an abnormality of a molecule secreted from vascular endothelial cells.

[R] The use according to the above [Q], wherein the disease caused by an abnormality of a molecule secreted from vascular endothelial cells is hemophilia A, hemophilia B, von Willebrand disease, hypertension, impaired glucose tolerance, lipid metabolism disorder, metabolic syndrome or osteoporosis.

[S] A method for treating a disease, the method comprising the step of administering the cell population according to the above [4] or the vascular endothelial stem cell according to the above [7] to improve the disease by a transgene product produced from the cells.

[T] The cell population according to the above [4] or the vascular endothelial stem cell according to the above [7] for use in treatment of a disease improved by a transgene product produced from the cells.

[U] Use of the cell population according to the above [4] or the vascular endothelial stem cell according to the above [7] for production of a medicament for treating a disease improved by a transgene product produced from the cells.

EXAMPLES

The present invention will be described in more detail below with reference to Examples, but the present invention is not limited thereto.

Example 1: Identification of Vascular Endothelial Stem Cells by Cell Surface Markers in Mouse Liver SP and MP cell populations were collected from vascular endothelial cells ($CD31^+CD45^-$ cells) in mouse livers. Genes expressed higher in the SP cell population than in the MP cell population were comprehensively analyzed, and as a result, more than 100 genes were identified. The cell surface markers of vascular endothelial stem cells, consisting of about 10% of the SP cell population, were attempted to be identified from these genes.

1-1 Surface Marker Analysis of Vascular Endothelial Cells in Mouse Liver
(1) Animals Used and Cell Preparation C57BL/6 mice and C57BL/6-Tg (CAG-EGFP) mice (commonly known as green mice) were purchased from Japan SLC, Inc. Mice at 8 to 12 weeks of age were used for experiments. The abdomen of the mice was dissected under anesthesia and the livers were harvested. The livers were cut into small pieces and immersed in a mixed solution of dispase II (Roche Applied Science), collagenase (Wako) and type II collagenase (Worthington Biochemical Corp.) at 37° C. with shaking to allow for the digestion of the extracellular matrix. The digested liver was passed through a filter of 40 μm pore size to prepare a dissociated cell suspension. Erythrocytes were lysed with ACK (Ammonium-Chloride-Potassium) solution (0.15 M $NH_4Cl$, 10 mM $KHCO_3$ and 0.1 mM $Na_2$-EDTA), and the remaining cells were used for experiments.

(2) Immunofluorescence Staining and Flow Cytometric Analysis

Immunofluorescence staining was performed on the cells prepared in the above (1), and the cells were analyzed by flow cytometry. The monoclonal antibodies used in immunofluorescence staining were anti-CD31 (clone MEC 13.3, BD Biosciences), anti-CD45 (clone 30-F11, BD Biosciences), anti-CD157 (clone BP3, Biolegend) and anti-CD200 (clone OX90, Biolegend) antibodies. Propidium iodide (PI, 2 μg/mL, Sigma-Aldrich) was added to the stained cells to exclude dead cells before flow cytometric analysis. For flow cytometric analysis, a FACSAria II SORP cell sorter (BD Bioscience) and FlowJo software (Treestar Software) were used.

(3) Results

The results are shown in FIGS. 1A and 1B. The cells in the boxed region ($CD31^+CD45^-$ cells) in the dot plot in FIG. 1A were collected as vascular endothelial cells in the livers. Expression levels of CD157 (X-axis) and CD200 (Y-axis) in the collected cells were analyzed, and the results are shown in the dot plot in FIG. 1B. Based on the results, the vascular endothelial cells in the livers were found to be divided into three fractions: fraction A of $CD157^+CD200^+$, fraction B of $CD157^-CD200^+$ and fraction C of $CD157^-CD200^-$. Each of the fractions was collected and used for experiments as follows.

1-2 Colony-Forming Assays of Cells Fractionated Based on Expression of CD157 and CD200
(1) Experimental Method The cells of fraction A ($CD157^+CD200^+$), fraction B ($CD157^-CD200^+$) and fraction C ($CD157^-CD200^-$) were seeded in 24-well culture plates. OP9 stromal cells (RIKEN cell bank) were seeded as feeder cells at 5000 cells/well. Cultures were maintained in RPMI medium (Sigma-Aldrich Japan) supplemented with 10% FCS and VEGF (10 ng/ml, PeproTech). After 10 days, the cells in each well were fixed and stained with an anti-CD31 antibody (BD Biosciences).

The cell population of fraction A corresponds to the second cell population of the present invention, and a mixed cell population of fractions A and B corresponds to the first cell population of the present invention.

(2) Results

The results are shown in FIG. 2. The results of fractions A, B and C are shown in the right, middle and left panels, respectively. The CD157$^+$CD200$^+$ cells of fraction A formed a great number of larger CD31$^+$ colonies. The CD157$^-$CD200$^+$ cells of fraction B possessed a colony-forming ability, but the size and number of colonies were smaller than those of the colonies formed from the cells of fraction A. The CD157$^-$CD200$^-$ cells of fraction C survived as CD31$^+$ cells, but most of the cells lost their colony-forming ability. The results indicate that CD157$^+$CD200$^+$ cells (fraction A) are vascular endothelial stem cells. Also indicated is that vascular endothelial differentiation starts from these CD157$^+$CD200$^+$ cells (fraction A) that give rise to CD157$^-$CD200$^+$ cells (fraction B) corresponding to vascular endothelial progenitors that partially retain their stem cell potential, and ends at terminally differentiated mature CD157$^-$CD200$^-$ vascular endothelial cells. That is, the second cell population of the present invention was assumed to be a cell population mainly composed of vascular endothelial stem cells, and the first cell population of the present invention was assumed to be a mixed cell population of vascular endothelial stem cells and vascular endothelial progenitor cells that partially retain their stem cell potential.

1-3 Investigation of Stem Cell Potential Using Liver Vascular Injury Model Mice (1) Liver Vascular Injury Model Mice To produce a mouse model of liver vascular injury, monocrotaline (Sigma-Aldrich) was intraperitoneally administered to C57BL/6 mice at a dose of 300 mg/kg, and whole body irradiation was performed on the same day at a dose of 30 rads/g.

(2) Experimental Method

The cells of fraction A (CD157$^+$CD200$^+$), fraction B (CD157$^-$CD200$^+$) and fraction C (CD157$^-$CD200$^-$) were collected from the livers of C57BL/6-Tg (CAG-EGFP) mice and used for experiments. The 2×10$^4$ cells of each fraction were separately transplanted into the livers of the liver vascular injury model mice via the splenic vein. Four weeks after transplantation, the abdomen of the mice was dissected under anesthesia, and the livers were observed under a fluorescence stereomicroscope (Leica). The livers were then harvested and cell suspensions were prepared in the same manner as in the above 1-1 (1). Immunofluorescence staining was performed with anti-CD31, anti-CD157 and anti-CD200 antibodies, and the cells were analyzed by flow cytometry.

(3) Results

The results are shown in FIG. 3. The left panels are fluorescence stereomicroscopic images of the livers. The liver transplanted with the CD157$^+$CD200$^+$ cells of fraction A (upper panel) had a much larger GFP-positive area, indicating that the GFP-positive transplanted cells gave rise to numerous vascular regions. The liver transplanted with the CD157$^-$CD200$^+$ cells of fraction B (middle panel) had a smaller GFP-positive area than that of the liver transplanted with the cells of fraction A. That is, the cells of fraction B retained the capacity to generate vascular regions, but their capacity was lower than that of the cells of fraction A. In the liver transplanted with the CD157$^-$CD200$^-$ cells of fraction C (lower panel), the transplanted cells were observed to only survive as GFP-positive cells, indicating that the cells of fraction C had no capacity to generate new vascular regions.

GFP-positive CD31$^+$ cells (the cells derived from the transplanted cells) (center panels) were collected from the livers transplanted with the cells of the fractions. Dot plots were generated by plotting the CD157 expression level (X-axis) and the CD200 expression level (Y-axis) in the collected cells and are shown in the right panels. In the liver transplanted with CD157$^+$CD200$^+$ cells of fraction A (upper panel), CD157$^+$CD200$^+$ cells differentiated into CD157$^-$CD200$^+$ cells and further into CD157$^-$CD200$^-$ cells. In the liver transplanted with CD157$^-$CD200$^+$ cells of fraction B (middle panel), the cells differentiated into CD157$^-$CD200$^-$ cells. In the liver transplanted with CD157$^-$CD200$^-$ cells of fraction C (lower panel), the transplanted cells survived as GFP-positive cells.

1-4 Summary

As a result of analysis of vascular endothelial cells (CD31$^+$CD45$^-$ cells) fractionated by CD157 and CD200 expression, CD157$^+$CD200$^+$ vascular endothelial cells were found to serve as stem cells that robustly contribute to blood vessel formation. CD157$^-$CD200$^+$ cells derived from CD157$^+$CD200$^+$ vascular endothelial stem cells retain their still proliferation potential although their proliferation potential is inferior to that of stem cells. In other words, the CD157$^-$CD200$^+$ cells appeared to act as the so-called vascular endothelial progenitor cells that partially retain their stem cell potential. CD157$^-$CD200$^-$ cells derived from CD157$^-$CD200$^+$ vascular endothelial progenitor cells were assumed to be terminally differentiated vascular endothelial cells with very low proliferative activity. Based on the study results, the inventors found for the first time in the world that a hierarchy of vascular endothelial cells exists, and that vascular system cells are committed to a lineage of differentiation starting from vascular endothelial stem cells that give rise to vascular endothelial progenitor cells and ending at terminally differentiated vascular endothelial cells.

Although the data are not shown, the inventors also confirmed that blood vessels formed from the transplanted CD157$^+$CD200$^+$ cells in mice survived without reduction even one year after transplantation.

Example 2: Treatment of Hemophilia by Transplantation of CD157$^+$CD200$^+$ Vascular Endothelial Cells Stem cells maintain their undifferentiated state, and continuously replicate themselves and differentiate into terminally differentiated somatic cells. In view of this fact, transplantation of CD157$^+$CD200$^+$ cells, presumably serving as vascular endothelial stem cells, is expected to result in continuous production of vascular endothelial cells over a long period of time. Further, transplantation of CD157$^+$CD200$^+$ cells into patients with a disease caused by the malfunction of vascular endothelial cells would be able to completely cure the disease. Accordingly, we investigated whether transplantation of normal CD157$^+$CD200$^+$ cells into the livers of hemophilia A model mice can reduce the bleeding tendency of the mice.

(1) Experimental Method

Hemophilia A model mice (coagulation factor VIII gene-deficient mice) were purchased from the Jackson Laboratory. CD157$^+$CD200$^+$ vascular endothelial cells and CD157–CD200– vascular endothelial cells were prepared from the livers of C57BL/6-Tg (CAG-EGFP) mice in the same manner as in the above 1-1 of Example 1. The CD157$^+$CD200$^+$ vascular endothelial cells and the CD157$^-$CD200$^-$ vascular endothelial cells isolated from the C57BL/6-Tg mice were separately transplanted into the livers of the hemophilia A model mice via the splenic vein, and the blood was collected to obtain the plasma 6 weeks after transplantation. The blood was also collected from wild-type mice, coagulation factor VIII gene-heterozygous deficient mice, and coagulation factor VIII gene-deficient mice with no cell transplantation to obtain the plasma. The coagulation factor VIII in the plasma was measured with Thrombocheck FVIII kit (Sysmex Corporation).

The livers were harvested under anesthesia by dissecting the abdomen of the hemophilia A model mice transplanted with the CD157$^+$CD200$^+$ endothelial vascular cells and the hemophilia A model mice transplanted with the CD157–CD200– vascular endothelial cells 6 weeks after transplantation. The cryosections were prepared from the harvested livers in a conventional manner, stained with anti-EGFP and anti-CD31 antibodies, and observed under a fluorescent microscope for the presence of EGFP$^+$CD31$^+$ cells. Tails of the hemophilia A model mice transplanted with the CD157$^+$CD200$^+$ vascular endothelial cells and the hemophilia A model mice with no cell transplantation were clipped, and the blood oozed from the tails was blotted on a filter paper every minute to record the time to stop bleeding.

(2) Results

Figure 4:
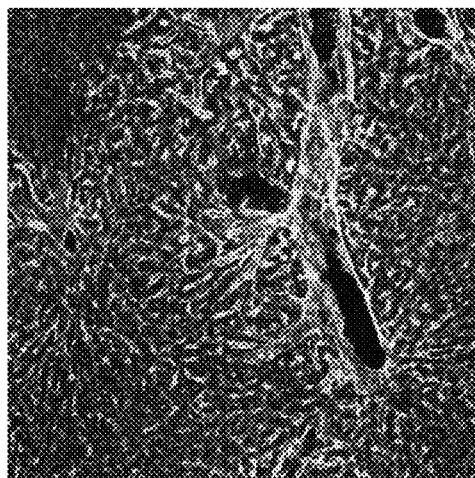
FIG. 4 shows a microscopic image of a cryosection of the liver of a hemophilia A model mouse transplanted with $CD157^+CD200^+$ vascular endothelial cells, stained with anti-EGFP and anti-CD31 antibodies.

FIG. 4 shows a fluorescence microscopic image of a cryosection of the liver of the hemophilia A model mice transplanted with the CD157$^+$CD200$^+$ vascular endothelial cells, stained with anti-EGFP and anti-CD31 antibodies. The observations revealed that the transplanted EGFP-positive vascular endothelial cells gave rise to blood vessels, and EGFP-positive blood vessels replaced the sinusoidal vascular network.

FIG. 5 shows the measurement results of the plasma coagulation factor VIII activity (N=4, Student's t test). The measured activities are shown as relative values to the measured activity of coagulation factor VIII in a standard plasma, which was taken as 100%. No coagulation factor VIII activity was detected in the plasma of the hemophilia A model mice. On the contrary, the coagulation factor VIII activity was detected in the hemophilia A model mice transplanted with the CD157$^+$CD200$^+$ vascular endothelial cells, and determined to be about 70% of that of wild-type mice. This coagulation factor VIII activity was higher than that in the coagulation factor VIII gene-heterozygous deficient mice. However, expression of the coagulation factor VIII was not substantially improved in the hemophilia A model mice transplanted with CD157$^-$CD200$^-$ vascular endothelial cells.

FIGS. 6A and 6B show the bleeding time in the hemophilia A model mice transplanted with the CD157$^+$CD200$^+$ vascular endothelial cells and the hemophilia A model mice with no cell transplantation. FIG. 6A shows the measurement results in the hemophilia A model mice with no cell transplantation, and FIG. 6B shows the measurement results of the hemophilia A model mice transplanted with the CD157$^+$CD200$^+$ vascular endothelial cells. In the hemophilia A model mice with no cell transplantation, bleeding continued for 60 minutes or more, whereas bleeding stopped a little less than 5 minutes in the hemophilia A model mice transplanted with the CD157$^+$CD200$^+$ vascular endothelial cells.

The results indicate that transplantation of the CD157$^+$CD200$^+$ vascular endothelial cells (vascular endothelial stem cells) is effective for the treatment of a disease caused by the malfunction of vascular endothelial cells.

Example 3: Liver Regeneration by Transplantation of CD157$^+$CD200$^+$ Vascular Endothelial Cells Molecules secreted from vascular endothelial cells have essential functions for maintenance of tissue homeostasis and tissue reconstruction, as recently described. Vascular endothelial cells residing in liver sinusoidal vessels have also been described to take part in the mechanisms of maintenance of hepatocytes. Based on the above experimental results demonstrating that the CD157$^+$CD200$^+$ vascular endothelial cells robustly contribute to the formation of liver sinusoidal vessels, we investigated whether transplantation of CD157$^+$CD200$^+$ vascular endothelial cells can promote liver regeneration.

3-1 Liver Regeneration Experiment 1

(1) Experimental Method

C57BL/6 mice were subjected to 70% partial hepatectomy in a conventional manner. CD157$^+$CD200$^+$ vascular endothelial cells and CD157$^-$CD200$^-$ vascular endothelial cells were prepared from the livers of C57BL/6-Tg (CAG-EGFP) mice in the same manner as in the above 1-1 of Example 1. The CD157$^+$CD200$^+$ vascular endothelial cells and the CD157$^-$CD200$^-$ vascular endothelial cells were separately transplanted into the livers of the 70% partially hepatectomized mice via the splenic vein, and the livers were harvested from the mice under anesthesia to measure the weight of the livers 8 days after transplantation.

(2) Results

Although the data are not shown, liver regeneration was more strongly promoted in the mice transplanted with the CD157$^+$CD200$^+$ vascular endothelial cells than in the mice transplanted with CD157$^-$CD200$^-$ vascular endothelial cells. The results demonstrate that transplantation of CD157$^+$CD200$^+$ vascular endothelial cells (vascular endothelial stem cells) is effective for the treatment of diseases such as hepatic fibrosis and cirrhosis.

3-2 Liver Regeneration Experiment 2

(1) Experimental Method

A cell suspension was prepared from the livers of C57BL/6-Tg (CAG-EGFP) mice in the same manner as in the above 1-1 (1) of Example 1. The cells were subjected to Hoechst staining and immunofluorescence staining, followed by flow cytometric analysis. For Hoechst staining, the cell suspension at 1×10$^6$ cells/mL was incubated with Hoechst stain solution (DMEM (Sigma-Aldrich) supplemented with 2% FBS (Sigma-Aldrich), 1 mM HEPES (Gibco) and 5 µg/mL Hoechst 33342 (Sigma-Aldrich)) at 37° C. for 90 minutes. For immunofluorescence staining, the same anti-CD31 and anti-CD45 monoclonal antibodies as those in Example 1 were used. PI (2 µg/mL, Sigma-Aldrich) was added to the stained cells to exclude dead cells. CD31$^+$CD45$^-$PI$^-$ cells (vascular endothelial cells excluding dead cells) were collected, and Hoechst analysis was performed with a flow cytometer. For flow cytometric analysis, a FACSAria II SORP cell sorter (BD Bioscience) and FlowJo software (Treestar Software) were used. CD31$^+$CD45$^-$Hoechst$^-$ cells were collected as an SP cell population, and CD31$^+$CD45-Hoechst$^+$ cells were collected as an MP cell population. The inventors have confirmed that CD157$^+$CD200$^+$ cells account for about 70% of the SP cell population, whereas almost no CD157$^+$CD200$^+$ cells are contained in the MP cell population.

C57BL/6 mice were subjected to 70% partial hepatectomy in a conventional manner. Then 2×10$^4$ cells of each of the SP and MP cell populations were separately transplanted into the livers of the 70% partially hepatectomized mice via the splenic vein. The livers were harvested from the mice under anesthesia for measurement of the weight 7 days after transplantation and observed under a fluorescent microscope.

GFP-positive vascular endothelial cells (GFP+CD31+ CD45− cells) were prepared from the harvested livers in the same manner as in the above 1-1 of Example 1. Total RNAs were prepared from the GFP-positive vascular endothelial cells isolated after transplantation and from the SP population cells before transplantation ($1\times10^4$ cells each) using RNAeasy kit (Qiagen). Then CDNAs were synthesized using ExScript RT reagent Kit (Takara Bio). Real-time PCR was performed on the CDNAs obtained before and after transplantation (Pre and Post) to analyze the mRNA expression levels of Wnt2 and HGF. This mRNA expression analysis was based on the fact that liver vascular endothelial cells secrete cytokines including Wnt2 and HGF to the liver, and thereby contribute to prolonged maintenance of hepatocytes or liver regeneration. As a control, the mRNA expression level of the glycolytic pathway enzyme GAPDH (glyceraldehyde-3-phosphate dehydrogenase) was measured. The real-time PCR was performed on a Stratagene MX3000P system (Stratagene). The primers used in the real-time PCR were as follows.

```
Wnt2
                                         (SEQ ID NO: 1)
5'-AAGGACAGCAAAGGCACCTT-3'

(SEQ ID NO: 2)
5'-GAGCCACTCACACCATGACA-3'

HGF
                                         (SEQ ID NO: 3)
5'-ACCCTGGTGTTTCACAAGCA-3'

(SEQ ID NO: 4)
5'-CAAGAACTTGTGCCGGTGTG-3'

GAPDH
                                         (SEQ ID NO: 5)
5'-AACTTTGGCATTGTGGAAGG-3'

(SEQ ID NO: 6)
5'-GGATGCAGGGATGATGTTCT-3'
```

(2) Results

FIGS. 7A and 7B show the observed fluorescence microscopic images. FIG. 7A shows a fluorescence microscopic image of the liver transplanted with the SP population cells, and FIG. 7B shows a fluorescence microscopic image of the liver transplanted with the MP population cells. Blood vessel formation was achieved by the GFP-positive cells in the liver transplanted with the SP population cells, whereas the GFP-positive cells were almost absent from the liver transplanted with the MP population cells.

FIG. 8 shows the measurement results of the liver weight (N=6, Student's t test). The weight of the liver transplanted with the SP population cells was heavier than the liver transplanted with the MP population cells, indicating that liver regeneration was promoted by transplantation of the SP population cells.

FIGS. 9A and 9B show the mRNA expression levels of Wnt2 and HGF in the SP population cells before transplantation and in the GFP+CD31+CD45− vascular endothelial cells after transplantation of the SP population cells (N=3, Student's t test). FIGS. 9A and 9B show the mRNA expression levels of Wnt2 and HGF, respectively. The expression levels of Wnt2 and HGF increased after transplantation of the SP population cells (Post) as compared with before transplantation (Pre).

The results demonstrate that transplantation of vascular endothelial stem cells into the liver is effective for the treatment of diseases such as hepatic fibrosis and cirrhosis.

Example 4: CD157+CD200+ Vascular Endothelial Cells in Other Organs than Liver

The above experiments confirmed that organ-resident vascular endothelial stem cells can be isolated from the liver using CD31+, CD45−, CD157+ and CD200+ as markers. Based on the results, we investigated whether such vascular endothelial stem cells are present in other organs than the liver.

(1) Experimental Method

Retina, brain, heart, skin, muscles and lung were harvested from 8-week-old C57BL/6 mice. Cell suspensions were prepared from each organ in the same manner as in the above 1-1 (1) of Example 1. The cell suspensions were immunofluorescence stained with anti-CD31, anti-CD45, anti-CD157 and anti-CD200 antibodies to collect CD31+ CD45− CD157+CD200+ cells (CD157+CD200+ vascular endothelial cells) and CD31+CD45−CD157−CD200− cells (CD157−CD200− vascular endothelial cells). Colony-forming assays were performed on these cells in the same manner as in the above 1-2 (1) of Example 1.

(2) Results

The results are shown in FIGS. 10A to 10F. FIGS. 10A, 10B, 10C, 10D, 10E and 10F show microscopic images of the retina, brain, heart, skin (dermis), muscle tissue and lung, respectively. CD157+CD200+ vascular endothelial cells were able to be collected from each organ, and the cells formed a great number of large-sized CD31+ colonies. However, CD157−CD200− vascular endothelial cells possess poor colony-forming ability.

Blood vessels maintain the distinctive structure in various organs and support the functions of the organs. Vascular endothelial stem cells in various organs could induce regeneration of the organs.

Example 5: Transplantation of Gene-Transduced Vascular Endothelial Stem Cells

We investigated whether transplantation of gene-endothelial stem cells can induce transduced vascular continuous and persistent expression of a product of the transgene in the transplanted vascular endothelial stem cells and in vascular endothelial cells differentiated therefrom.

(1) Experimental Method

CD157+CD200+ vascular endothelial cells were prepared from the livers of C57BL/6-Tg (CAG-EGFP) mice in the same manner as in the above 1-1 of Example 1. Then 200 cells of the CD157+CD200+ vascular endothelial cells were suspended in 4000 μL of 4% fetal bovine serum (FBS, Sigma-Aldrich)-containing phosphate-buffered saline (PBS, Thermo Fisher) supplemented with 10 ng/mL VEGF. The cell suspension was dispensed at 20 μL per well into 96-well plates (Thermo Fisher) using a PIPETMAN (trade name, GILSON). Wells containing a single cell were selected by macroscopic inspection under a microscope (DM IL LED, Leica), and GFP expression was confirmed under a fluorescent microscope (DMi8, Leica).

Recipient mice were C57BL/6 mice (Japan SLC). A volume of 20 μL of the solution containing a single CD157+ CD200+ vascular endothelial cell was directly injected into the livers of the recipient mice via subcutaneous route using a syringe with an injection needle. One month after injection, the abdomen of the recipient mice was dissected under anesthesia, and the livers were observed under a fluorescence stereomicroscope (MZ 16 FA, Leica). The mice were euthanized and the livers were harvested. The areas containing GFP-positive vascular colonies were excised under a microscope and analyzed by fluorescence immunostaining and flow cytometric analysis. For fluorescence immunostaining, the specimens were fixed in 4% paraformaldehyde (Wako), stained with anti-GFP (MBL) and anti-CD31 (Clone 30-F11, BD Biosciences) antibodies followed by nuclear staining using SYTOX orange (Thermo Fisher), and observed under a confocal microscope (Leica). The cell suspension was prepared in the same manner as in the above 1-1 (1) of Example 1, and the flow cytometric analysis was performed in the same manner as in the above 1-1 (2) of Example 1.

(2) Results

FIG. 11 shows a fluorescence stereomicroscopic image of the liver of the recipient mice. The vascular structures maintaining the expression of GFP were observed.

FIGS. 12A and 12B show confocal microscopic images of the immunofluorescence stained livers of the recipient mice. FIG. 12A shows sections stained with the anti-GFP antibody, and FIG. 12B shows sections stained with the anti-CD31 antibody. Higher magnifications of areas (around the sinusoid) indicated by the dotted boxes in the top panels are shown in the bottom panels. CD31$^+$ cells expressing GFP were observed.

Figures 13A, 13B:
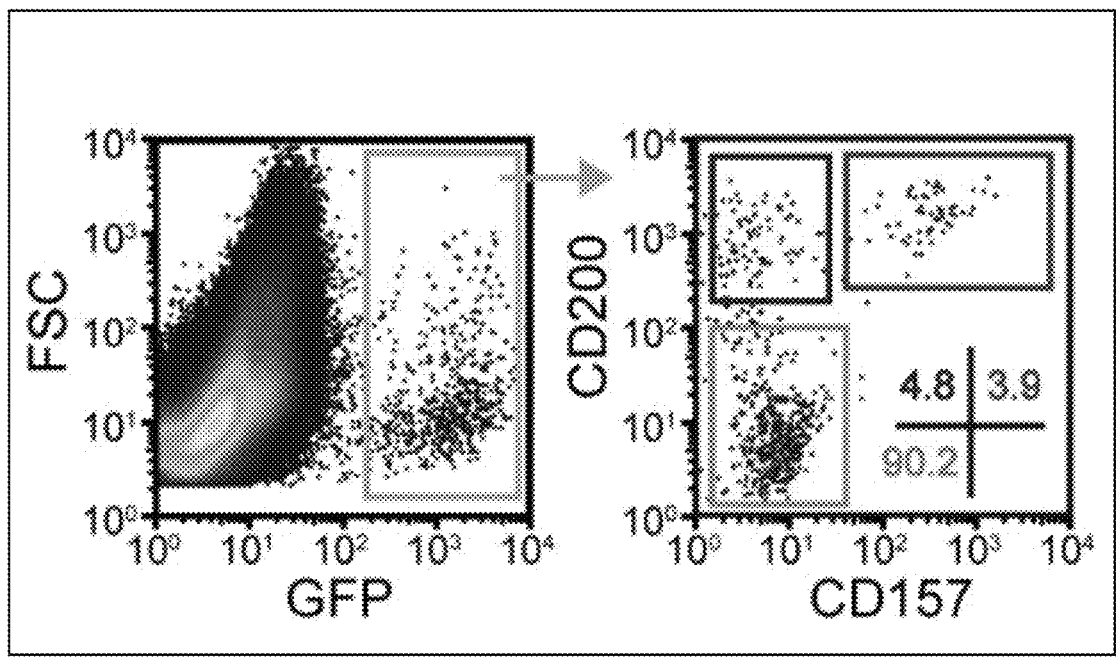
FIG. 13A shows the results of flow cytometric analysis of forward scatter (FSC) of an anti-GFP antibody-stained cell suspension prepared from the livers of the recipient mice of FIG. 11.
FIG. 13B shows the results of flow cytometric analysis of the cells in the boxed region (GFP-positive cells) in FIG. 13A, stained with anti-CD157 and anti-CD200 antibodies.

FIG. 13 shows the results of the flow cytometric analysis. The results indicate the presence of a great number of GFP-positive vascular endothelial cells (CD157$^-$CD200$^-$). The results also indicate proliferation of GFP-positive vascular endothelial stem cells (CD157$^+$CD200$^+$).

The results prove that even a single vascular endothelial stem cell, once resides in a living body, can maintain itself as a vascular endothelial stem cell and as a vascular endothelial cell in the body over a long period of time. The results also prove that, when vascular endothelial stem cells transduced with a gene encoding a molecule of interest useful for the treatment of a disease is transplanted into a living body to allow for secretion of the molecule from the cells, the molecule is able to be expressed in the body over a long period of time.

Example 6: Identification of Vascular Endothelial Stem Cells in Human Liver

Figures 14A, 14B:
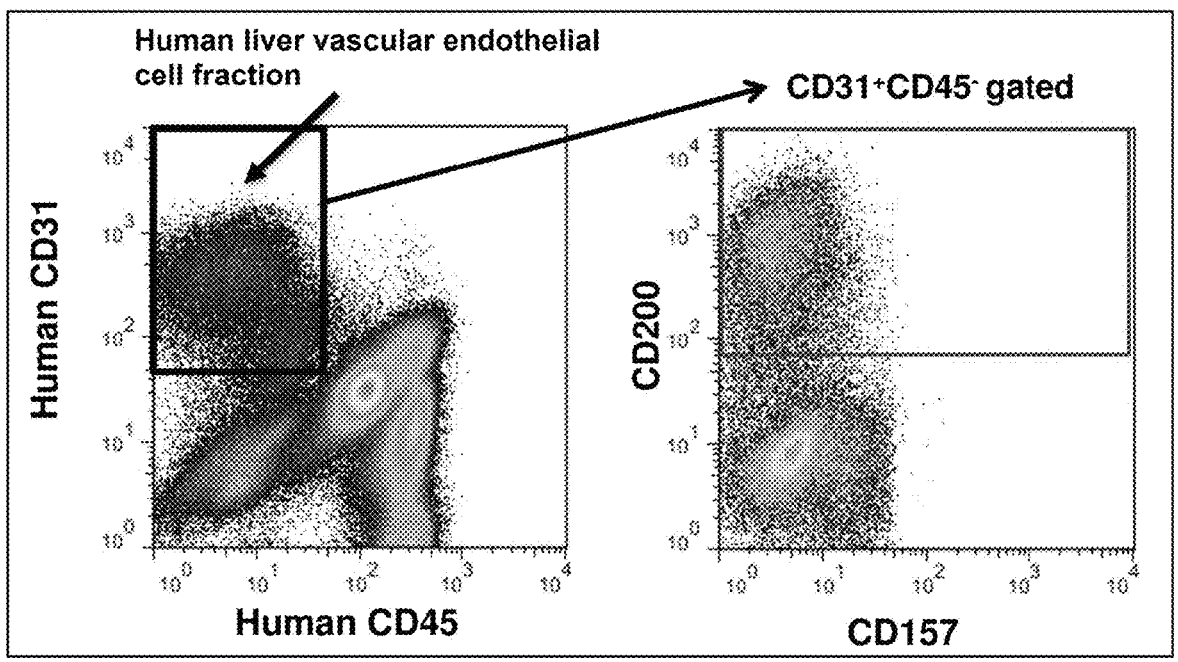
FIGS. 14A and 14B show the results of flow cytometric analysis of immunofluorescence stained human liver cells prepared by digestion and dissociation of human liver tissue.

We investigated whether vascular endothelial stem cells found in the livers of mice can also be identified in humans.
6-1 Surface Marker Analysis of Vascular Endothelial Cells in Human Liver
(1) Experimental Method A cell suspension was prepared from human liver tissue in the same manner as in the above 1-1 (1) of Example 1. Immunofluorescence staining was performed on the prepared cells, and the cells were analyzed by flow cytometry, in the same manner as in the above 1-1 (2) of Example 1.
(2) Results The results are shown in FIGS. 14A and 14B. The cells in the boxed region (CD31$^+$CD45$^-$ cells) in the dot plot in FIG. 14A were collected as vascular endothelial cells in the liver. Expression levels of CD157 (X-axis) and CD200 (Y-axis) in the collected cells were analyzed, and the results are shown in the dot plot in FIG. 14B. As shown in FIG. 14B, vascular endothelial cells (CD31$^+$CD45$^-$ cells) in human liver were found to be divided into two fractions, CD200$^-$ and CD200$^+$ fractions, based on the expression level of CD200. CD157$^+$ cells were also found to be present in human liver although the number is very small.

Figures 15A, 15B:
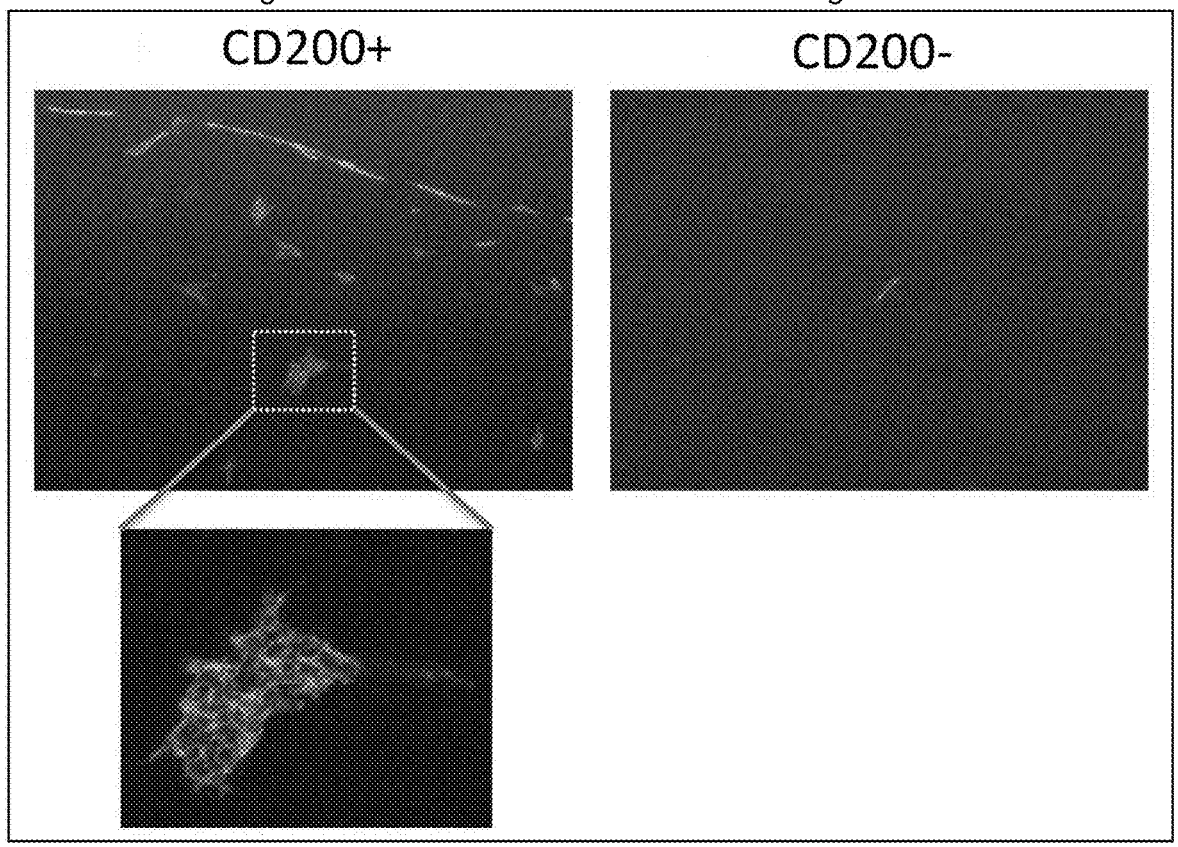
FIGS. 15A and 15B show the results of colony-forming assays of the cells of the CD200⁺ fraction (CD31⁺CD45⁻CD200⁺) and the CD200⁻ fraction (CD31⁺CD45⁻CD200⁻) as shown in FIG. 14B.

6-2 Colony-Forming Assays of Vascular Endothelial Cells Fractionated Based on Expression of CD200
(1) Experimental Method The CD200$^+$ fraction (the first cell population of the present invention: CD31$^+$CD45$^-$CD200$^+$ cells) and the CD200$^-$ fraction (CD31$^+$CD45$^-$CD200$^-$ cells) as shown in FIG. 14B were collected, and colony-forming assays were performed in the same manner as in the above 1-2 (1) of Example 1.
(2) Results The results are shown in FIGS. 15A and 15B. FIGS. 15A and 15B show the results of the assays on the CD200$^+$ fraction and the CD200$^-$ fraction, respectively. No CD31$^+$ colony-forming cells were present in the CD200$^-$ fraction as shown in FIG. 15B, whereas CD31$^+$ colony-forming cells were present in the CD200$^+$ fraction as shown in FIG. 15A. These results reveal that human n liver CD31$^+$CD45$^-$CD200$^+$ cells contain vascular endothelial stem cells with vascular endothelial colony-forming ability. In this Example, colony-forming assays were not performed on the CD157$^+$CD200$^+$ vascular endothelial cells (the second cell population of the present invention) because only a small number of the cells were obtained. However, as with a mouse CD157$^+$CD200$^+$ vascular endothelial cell population, a human CD157$^+$CD200$^+$ vascular endothelial cell population (the second cell population of the present invention) is expected to be mainly composed of vascular endothelial stem cells.

The above results indicate that vascular endothelial stem cells are commonly present in mammals and robustly contribute to blood vessel formation in various organs, and transplantation therapy using vascular endothelial stem cells could be effective for various diseases in humans.

Figures 16A, 16B:
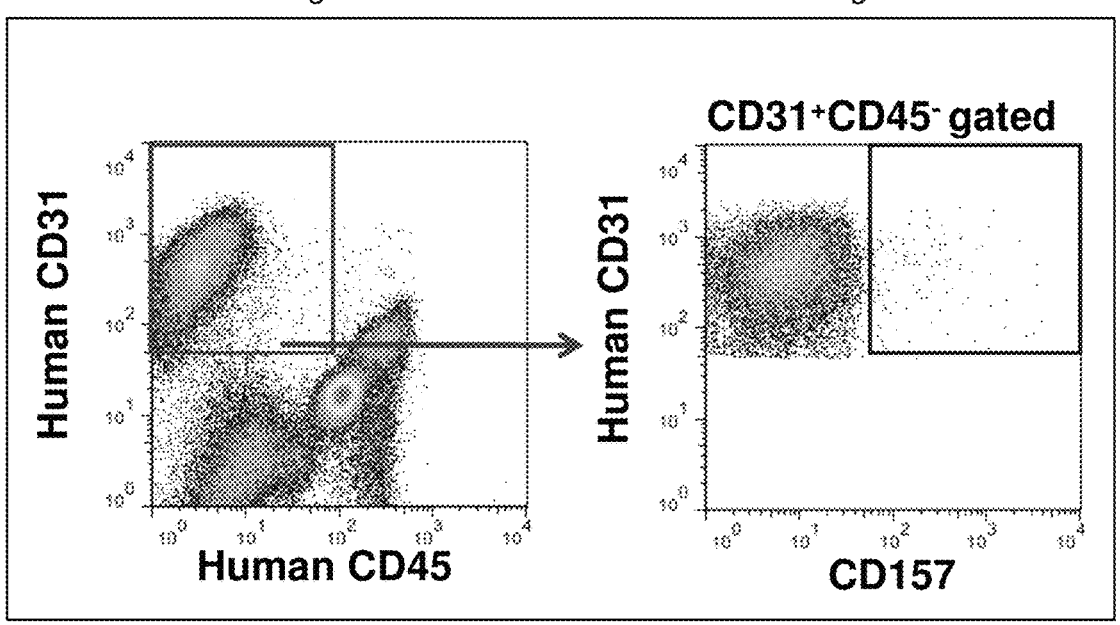
FIGS. 16A and 16B show the results of flow cytometric analysis of immunofluorescence stained human kidney cells prepared by digestion and dissociation of human kidney tissue.

Example 7: Identification of CD157-Positive Cells in Human Vascular Endothelial Cells Mouse vascular endothelial stem cells express CD157 in all the internal organs, organs and tissues (Example 4). In human liver, the presence of vascular endothelial stem cells in CD200$^+$ cell population was confirmed, but the presence of CD157$^+$ cells remained unclear. Accordingly, we investigated whether the presence of CD157$^+$ vascular endothelial cells can be confirmed in other human tissues than the liver.
(1) Experimental Method Cell suspensions were separately prepared from human kidney tissue and human placenta tissue in the same manner as in the above 1-1 (1) of Example 1. Immunofluorescence staining was performed on the prepared cells using anti-CD31 (clone WM59, BioLegend), anti-CD45 (clone HI30, BioLegend) and anti-CD157 (clone SY11B5, BD) antibodies, and the cells were analyzed by flow cytometry. For flow cytometric analysis, a FACSAria II SORP cell sorter (BD Bioscience) and FlowJo software (Treestar Software) were used.
(2) Experimental Results FIGS. 16A and 16B show the results of the flow cytometric analysis of the human kidney tissue, and FIGS. 17A and 17B show the results of the flow cytometric analysis of the human placenta tissue. FIGS. 16A and 17A show the results of the flow cytometric analysis of the tissues stained with the anti-CD31 and anti-CD45 antibodies. FIGS. 16B and 17B show the results of the flow cytometric analysis of CD157$^+$ cells in the boxed regions (CD31$^+$CD45$^-$ cells) in FIGS. 16A and 17A, respectively. The results of the flow cytometric analysis of the cells in the boxed regions (CD31⁺ CD45⁻ cells) in FIGS. 16A and 17A stained with the anti-CD157 antibody confirmed the presence of CD157⁺ vascular endothelial stem cell fraction in both of the kidney and placenta.

Example 8: Identification of SP Cell Population in Human Vascular Endothelial Cells The inventors have confirmed that side population cells (an SP cell population) are present in mouse vascular endothelial cells (non-patent literature 1). However, the presence of an SP cell population in vascular endothelial cells in human tissues has not been confirmed yet. Accordingly, we investigated whether the presence of an SP cell population in vascular endothelial cells can be confirmed in human tissues.

(1) Experimental Method

A cell suspension was prepared from human skin tissue in the same manner as in the above 1-1 (1) of Example 1. The cells were subjected to Hoechst staining and immunofluorescence staining, followed by flow cytometric analysis. For Hoechst staining, the cell suspension at $1 \times 10^6$ cells/mL was incubated with Hoechst stain solution (DMEM (Sigma-Aldrich) supplemented with 2% FBS (Sigma-Aldrich), 1 mM HEPES (Gibco) and 5 µg/mL Hoechst 33342 (Sigma-Aldrich)) at 37° C. for 90 minutes. For immunofluorescence staining, anti-CD31 (clone WM59, BioLegend) and anti-CD45 (Clone HI30, BioLegend) antibodies were used. PI (2 µg/mL, Sigma-Aldrich) was added to the stained cells to exclude dead cells. CD31⁺CD45⁻PI⁻ cells (vascular endothelial cells excluding dead cells) were collected, and Hoechst analysis was performed with a flow cytometer. For flow cytometric analysis, a FACSAria II SORP cell sorter (BD Bioscience) and FlowJo software (Treestar Software) were used.

(2) Experimental Results

The results are shown in FIG. 18. The results confirmed that an SP cell population fraction (indicated by the dotted box) is present in human skin tissue.

The present invention is not limited to each of the embodiments and Examples as described above, and various modifications are possible within the scope of the claims. Embodiments obtainable by appropriately combining the technical means disclosed in the different embodiments of the present invention are also included in the technical scope of the present invention. The contents of the scientific literature and the patent literature cited herein are hereby incorporated by reference in their entirety.

The invention claimed is:

1. A cell population comprising mammalian cells that are positive for cell surface markers CD31, CD157 and CD200 and negative for CD45.

2. The cell population according to claim 1, wherein the mammalian cells comprise vascular endothelial stem cells, which express a transgene.

3. The cell population according to claim 1, wherein the mammal is a human.

4. A mammalian vascular endothelial stem cell that is positive for the cell surface marker CD31, CD157 and CD200 and negative for CD45.

5. The mammalian vascular endothelial stem cell according to claim 4, wherein said vascular endothelial stem cell expresses a transgene.

6. The mammalian vascular endothelial stem cell according to claim 4, wherein the mammal is a human.

7. A method for evaluating vascular toxicity of a test substance, the method comprising:
   (1) culturing the cell population of claim 1 in a culture medium containing the test substance and in a culture medium free of the test substance,
   (2) measuring cell proliferation after culturing, and
   (3) comparing the amount of cell proliferation of the cell population cultured in the culture medium containing the test substance with the amount of cell proliferation of the cell population cultured in the culture medium lacking the test substance.

8. A method for preparing vascular endothelial stem cells, the method comprising:
   (I) digesting and dissociating an isolated organ to prepare a cell suspension, and
   (II) collecting cells that are positive for CD31, CD157 and CD200 and negative for CD45.

9. A method for regenerating blood vessels in a subject, comprising administering the cell population of claim 1 to said subject.

10. The method according to claim 9, wherein the cell population is administered to a subject having ischemia or undernutrition.

11. The method according to claim 9, wherein the cell population is administered to a subject having vascular malformation or blood flow impairment.

12. The method according to claim 9, wherein the cell population is administered to a subject needing organ regeneration.

13. The method according to claim 9, wherein the cell population is administered to a subject having an abnormal secretion of a molecule from vascular endothelial cells.

14. The method according to claim 13, wherein is the subject has hemophilia A, hemophilia B, von Willebrand disease, hypertension, impaired glucose tolerance, lipid metabolism disorder, metabolic syndrome or osteoporosis.

15. A method of therapy for a subject in need thereof comprising administering the cell population of claim 2 to said subject.

16. The method according to claim 15, wherein said subject has hemophilia A, hemophilia B, von Willebrand disease, a cancer, age-related macular degeneration, an autoimmune disease, rheumatism, dementia, diabetes mellitus, hypertension, diabetic nephropathy, osteoporosis, obesity or an infection.

* * * * *